US012605102B2

(12) United States Patent
Hori et al.

(10) Patent No.: US 12,605,102 B2
(45) Date of Patent: Apr. 21, 2026

(54) BIOLOGICAL SIGNAL PROCESSING DEVICE, WATCHING SYSTEM, AND WATCHING METHOD

(71) Applicant: Mitsubishi Electric Corporation, Tokyo (JP)

(72) Inventors: Junji Hori, Tokyo (JP); Ryo Saito, Tokyo (JP); Yoshiyuki Kanamaru, Tokyo (JP); Ken Imai, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 456 days.

(21) Appl. No.: 17/922,889

(22) PCT Filed: Jun. 5, 2020

(86) PCT No.: PCT/JP2020/022247
§ 371 (c)(1),
(2) Date: Nov. 2, 2022

(87) PCT Pub. No.: WO2021/245902
PCT Pub. Date: Dec. 9, 2021

(65) Prior Publication Data
US 2023/0165507 A1 Jun. 1, 2023

(51) Int. Cl.
*A61B 5/00* (2006.01)
*A61B 5/024* (2006.01)
(Continued)

(52) U.S. Cl.
CPC .......... *A61B 5/352* (2021.01); *A61B 5/02405* (2013.01); *A61B 5/0245* (2013.01); *A61B 5/7221* (2013.01)

(58) Field of Classification Search
CPC ... A61B 5/352; A61B 5/02405; A61B 5/0245; A61B 5/7221
See application file for complete search history.

(56) References Cited

U.S. PATENT DOCUMENTS

2001/0008954 A1* 7/2001 Levitan ................ A61B 5/0245
600/515
2008/0167567 A1* 7/2008 Bashour ................. A61B 5/352
600/521
(Continued)

FOREIGN PATENT DOCUMENTS

JP 2018094156 A 6/2018

OTHER PUBLICATIONS

International Search Report (PCT/ISA/210) with translation and Written Opinion (PCT/ISA/237) mailed on Sep. 1, 2020, by the Japan Patent Office as the International Searching Authority for International Application No. PCT/JP2020/022247. (11 pages).
(Continued)

*Primary Examiner* — Sana Sahand
(74) *Attorney, Agent, or Firm* — BUCHANAN, INGERSOLL & ROONEY PC

(57) ABSTRACT

An object is to provide a biological signal processing device capable of evaluating the reliability of the measurement state of a biological signal, based on RRI information. A biological signal processing device includes: an RRI information acquisition means for acquiring RRI information composed of RRIs, of a biological signal measured by a sensor, arranged in time series, from the sensor; a map generation means for plotting points whose positions are determined based on values of the RRIs constituting the RRI information, on a feature space, and generating a map from the feature space; an index calculation means for calculating an index indicating resemblance to heart rate variability of each RRI constituting RRI information to be evaluated; and a reliability calculation means for calculating RRI reliability of each RRI constituting the RRI information, from the index.

16 Claims, 12 Drawing Sheets

(51) Int. Cl.
    *A61B 5/0245*            (2006.01)
    *A61B 5/352*             (2021.01)

(56)                     References Cited

U.S. PATENT DOCUMENTS

2016/0094899 A1*   3/2016   Aumer ................. A61B 5/6815
                                                  340/870.07
2018/0296105 A1* 10/2018   Blake ..................... A61B 5/349

OTHER PUBLICATIONS

Office Action dated Apr. 23, 2024, issued in the corresponding
Canadian Patent Application No. 3,177,890, 5 pages.
Office Action dated Mar. 19, 2025, issued in the corresponding
Canadian Patent Application No. 3,177,890, 3 pages.

\* cited by examiner

ST101 — ACQUIRE RRI INFORMATION FOR LEARNING

ST102 — GENERATE MAP FROM ACQUIRED RRI INFORMATION

ST103 — ACQUIRE RRI INFORMATION OF TARGET TO BE WATCHED

ST104 — CALCULATE INDEX OF EACH RRI TO BE EVALUATED

ST105 — CALCULATE RRI RELIABILITY AND CORRECTION RRI INFORMATION

ST106 — DETERMINE WORN STATE OF SENSOR

ST107 — PERFORM HEART RATE VARIABILITY ANALYSIS

ST108 — DISPLAY ANALYSIS RESULT

START

ST301 — ACQUIRE RRI INFORMATION OF TARGET TO BE WATCHED

ST302 — GENERATE MAP FROM ACQUIRED RRI INFORMATION

ST303 — CALCULATE INDEX OF EACH RRI TO BE EVALUATED

ST304 — CALCULATE RRI RELIABILITY AND CORRECTION RRI INFORMATION

ST305 — DETERMINE WORN STATE OF SENSOR

ST306 — PERFORM HEART RATE VARIABILITY ANALYSIS

ST307 — DISPLAY ANALYSIS RESULT

END

BIOLOGICAL SIGNAL PROCESSING DEVICE, WATCHING SYSTEM, AND WATCHING METHOD

TECHNICAL FIELD

The present disclosure relates to a biological signal processing device, a watching system, and a watching method.

BACKGROUND ART

Conventionally, there have been watching systems that centrally manage the physical and mental states of workers in factories and the like, drivers who are driving vehicles, elderly people who live alone, etc. Some of these systems determine the state of a target to be watched, from a biological signal. In such a watching system, the reliability of a biological signal measured by a sensor is important. Conventionally, there has been a watching system that extracts R waves from a cardiac potential waveform, and evaluates the reliability of the measurement state of an instantaneous heart rate (RRI: R-R-interval), which is the interval between two R waves adjacent to each other in time series, according to the type of the measurement state of the two R waves (see, for example, Patent Document 1). In the technology described in Patent Document 1, the measurement state of each extracted R wave is determined on the basis of the potential information of each R wave, thereby evaluating the reliability of an RRI.

CITATION LIST

Patent Document

Patent Document 1: Japanese Laid-Open Patent Publication No. 2018-094156

SUMMARY OF THE INVENTION

Problems to be Solved by the Invention

The technology described in Patent Document 1 requires not only RRI information but also information about the shape of each R wave. However, among sensors that measure biological signals, many sensors output only RRI information and do not output a cardiac potential waveform itself. In the case where such a sensor is used in the above-described watching system, it is necessary to evaluate the reliability of the measurement state of a biological signal from only RRI information, but the technology described in Patent Document 1 cannot handle this evaluation.

The present disclosure has been made to solve the above problem, and an object of the present disclosure is to provide a biological signal processing device that is capable of evaluating the reliability of the measurement state of a biological signal on the basis of RRI information.

Another object of the present disclosure is to provide a watching system and a watching method that are capable of evaluating the reliability of the measurement state of a biological signal on the basis of RRI information and are capable of grasping the state of a target to be watched, from the RRI information.

Solution to the Problems

A biological signal processing device according to the present disclosure includes: an RRI information acquisition means for acquiring, from a sensor for calculating RRIs of a biological signal of a target to be watched, RRI information composed of a plurality of the RRIs arranged in time series; a map generation means for plotting a plurality of first points whose positions are determined on the basis of values of the RRIs in a normal state among the RRIs constituting the RRI information, on a feature space, and generating a map from the feature space on the basis of the plurality of first points; an index calculation means for plotting a second point whose position is determined by a value of each RRI to be evaluated, on the feature space, and calculating an index indicating resemblance to heart rate variability of each RRI to be evaluated, on the basis of a relationship between the second point and the map; and a reliability calculation means for calculating RRI reliability indicating reliability of each RRI to be evaluated, from the index.

Moreover, a watching system according to the present disclosure includes: a sensor for calculating RRIs of a biological signal of a target to be watched; an RRI information acquisition means for acquiring RRI information composed of a plurality of the RRIs arranged in time series; a map generation means for plotting a plurality of first points whose positions are determined on the basis of values of the RRIs in a normal state among the RRIs constituting the RRI information, on a feature space, and generating a map from the feature space on the basis of the plurality of first points; an index calculation means for plotting a second point whose position is determined by a value of each RRI to be evaluated, on the feature space, and calculating an index indicating resemblance to heart rate variability of each RRI to be evaluated, on the basis of a relationship between the second point and the map; a reliability calculation means for calculating RRI reliability indicating reliability of each RRI to be evaluated, from the index; an RRI information correction means for correcting the RRI information on the basis of the RRI reliability and outputting the RRI information as correction RRI information; a heart rate variability analysis means for analyzing heart rate variability of the target to be watched, on the basis of the correction RRI information; and an analysis result output means for outputting an analysis result by the heart rate variability analysis means.

Moreover, a watching method according to the present disclosure includes: a step of acquiring RRIs of a biological signal of a target to be watched, by a sensor, and acquiring RRI information composed of a plurality of the RRIs arranged in time series; a step of plotting a plurality of first points whose positions are determined on the basis of values of the RRIs in a normal state among the plurality of the RRIs, on a feature space, and generating a map from the feature space on the basis of the plurality of first points; a step of plotting a second point whose position is determined by a value of each RRI to be evaluated, on the feature space, and calculating an index indicating resemblance to heart rate variability of each RRI to be evaluated, on the basis of a relationship between the second point and the map; a step of calculating RRI reliability indicating reliability of each RRI to be evaluated, from the index; a step of correcting the RRI information on the basis of the RRI reliability to obtain correction RRI information; a step of analyzing heart rate variability of the target to be watched, on the basis of the correction RRI information; and a step of outputting an analysis result by the step of analyzing heart rate variability.

Effect of the Invention

The biological signal processing device according to the present disclosure is capable of evaluating the reliability of the measurement state of a biological signal on the basis of RRI information.

Moreover, the watching system according to the present disclosure is capable of evaluating the reliability of the measurement state of a biological signal on the basis of RRI information and is capable of grasping the state of a target to be watched, from the RRI information.

DESCRIPTION OF EMBODIMENTS

Embodiment 1

(Description of RRI Information)

Figure 1A:
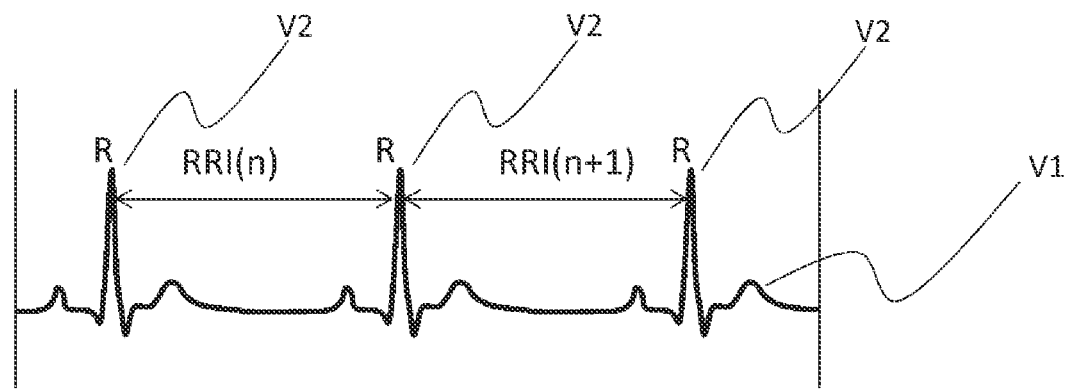
FIG. 1A shows a general cardiac potential waveform.

Embodiment 1 will be described with reference to FIG. 1A to FIG. 9B. The "target to be watched" in Embodiment 1 is a person who can be monitored or watched, such as a worker who performs work in a factory or the like, a driver who is driving a vehicle, and an elderly person who lives alone. First, RRI information treated in the present disclosure will be described with reference to FIG. 1A and FIG. 1B. FIG. 1A shows a general cardiac potential waveform, the horizontal axis represents time, and the vertical axis represents potential. In a cardiac potential waveform V1 shown in FIG. 1A, sharp peaks appear at intervals. These peak portions V2 are generally referred to as R waves. R waves are signal changes which occur reflecting ventricular excitation, and the interval between R waves adjacent to each other in time series is defined as an RRI. The RRI represents the time required for a single beat of the heart. Usually, R waves are extracted by peak detection, and the time intervals between the sequentially measured R waves are RRIs. The RRIs can be obtained as a series of time-sequence data from a cardiac potential waveform. In FIG. 1A, an RRI obtained at the nth time is denoted as RRI(n), and an RRI obtained at the n+1th time is denoted as RRI(n+1). Whereas a heart rate represents the number of heart beats per minute, the reciprocal of an RRI may be used as an instantaneous heart rate to finely grasp the variation of an exercise load. In addition, the appearance interval of R waves fluctuates under the control of the autonomic nerves. Therefore, the state of the autonomic nerves may be estimated by analyzing the temporal variation of the RRIs.

Figure 1B:
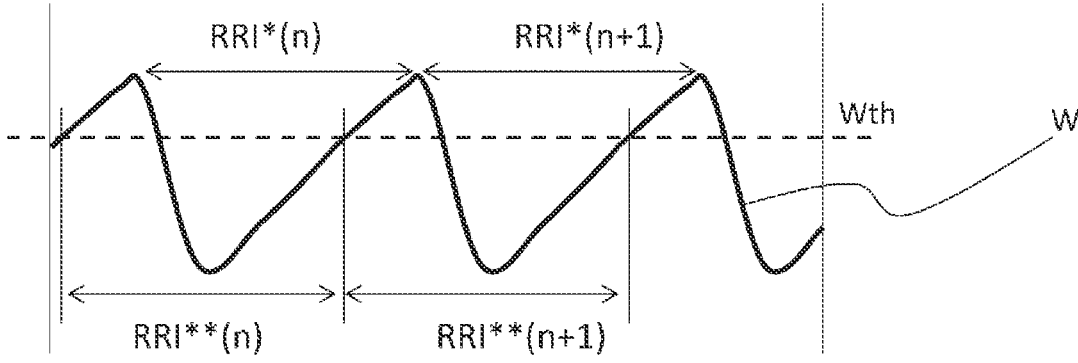
FIG. 1B shows a general pulse waveform.

As shown in FIG. 1B, similar to the cardiac potential waveform, a pulse wave W repeats a similar waveform every beat. Therefore, similar to the cardiac potential waveform, the equivalent of an RRI can be calculated for the pulse wave. For example, the interval between peaks adjacent to each other or the interval between valleys adjacent to each other can be treated in the same manner as an RRI. In FIG. 1B, the interval is denoted as RRI* to be distinguished from the RRI in the cardiac potential waveform. In addition, a threshold value Wth is set as shown by a dotted line in FIG. 1B, and it is also possible to treat the interval between timings of exceeding the threshold value Wth in the same manner as an RRI. The RRI in this case is represented as RRI** in FIG. 1B. In the following, the RRI in the cardiac potential waveform V1 will be described, but unless otherwise specified, the same applies to the RRI* and the RRI** in the pulse wave W.

(Omission of Detection and Erroneous Detection of R Waves)

Figure 2A:
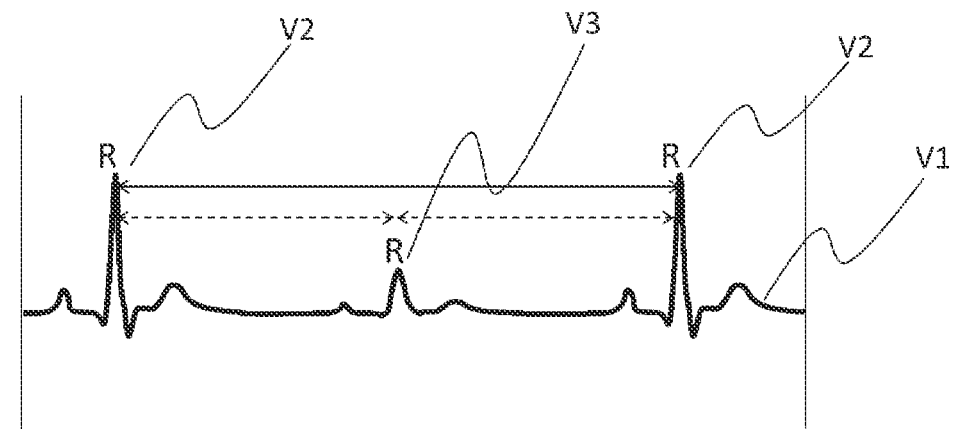
FIG. 2A shows a cardiac potential waveform in the case where omission of detection of an R wave occurs.
Figure 2B:
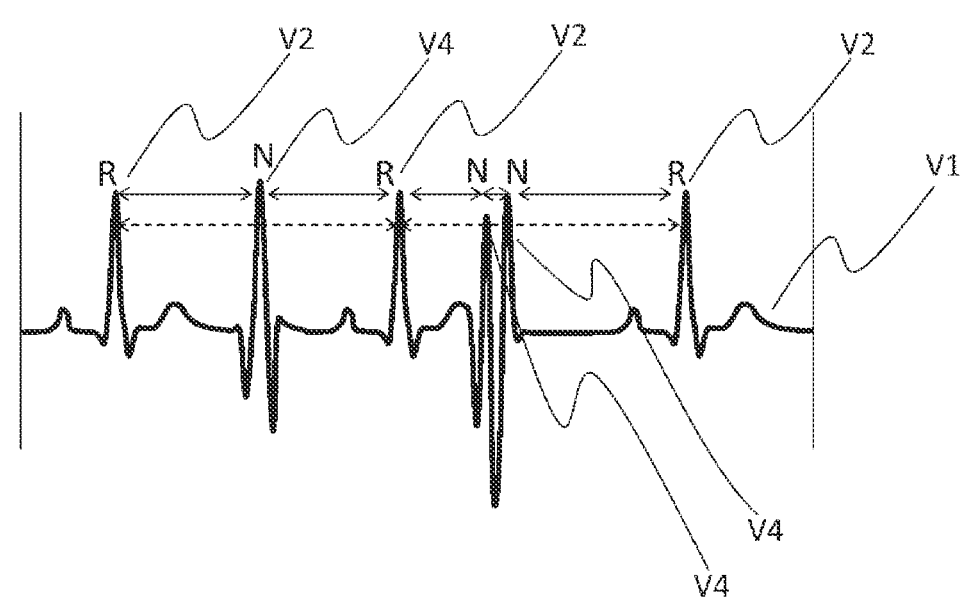
FIG. 2B shows a cardiac potential waveform in the case where erroneous detection of R waves occurs.

Omission of detection and erroneous detection of R waves in the case of using a cardiac potential waveform will be described with reference to FIG. 2A and FIG. 2B. In the case of acquiring a cardiac potential waveform or a pulse wave using a contact type sensor, signal detection may become unstable due to violent body movements or an abnormality in wearing of the sensor, resulting in loss of data of the cardiac potential waveform or mixing of noise in the cardiac potential waveform. For example, V3 shown in FIG. 2A is an R wave, but has a small peak potential and cannot be detected as an R wave. Therefore, in the cardiac potential waveform shown in FIG. 2A, omission of detection of an R wave occurs. In addition, noise V4 shown in FIG. 2B is not an R wave but is detected as an R wave. Therefore, in the cardiac potential waveform shown in FIG. 2B, erroneous detection of R waves occurs. In FIG. 2A and FIG. 2B, the RRI that should be measured is indicated by a dotted arrow, and the RRI that is actually measured is indicated by a solid arrow, and FIG. 2A and FIG. 2B show that RRIs are not accurately measured.

(Characteristics of RRI Information)

The characteristics of RRI information will be described with reference to FIG. 3. It is assumed that RRI information is represented as indicated by the following equation (1) from RRIs obtained in time series during a certain period.

[Math. 1]

$$RRI = \{RRI(1), RRI(2), \ldots RRI(i), RRI(i+1), \ldots RRI(N)\} \quad (1)$$

$$P_1 = (RRI(1), RRI(2))^T \quad (2)$$

-continued $$P_2 = (RRI(2), RRI(3))^T$$

$$P_{N-1} = (RRI(N-1), RRI(N))^T$$

$$P = (P_1, P_2, P_3, \ldots P_i, \ldots P_{N-1}) \qquad (3)$$

Figure 3:
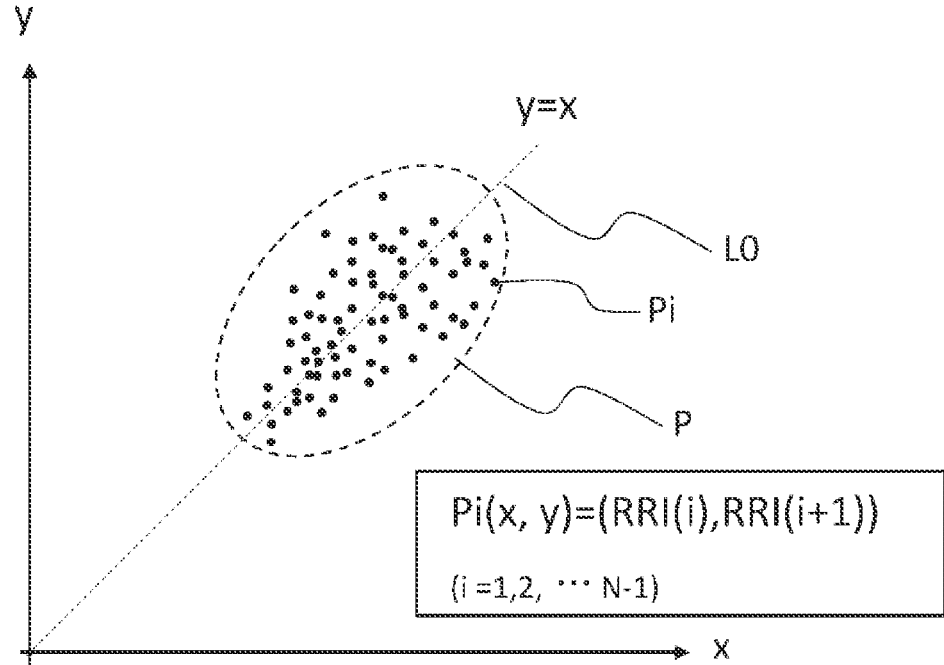
FIG. 3 illustrates the characteristics of general RRI information.

FIG. 3 is a plot of each point $P_i$ (i=1, 2, . . . N−1) constituting a point group P, on an xy plane, and illustrates the characteristics of general RRI information. That is, if the state of a target to be watched is normal during the period in which the RRIs constituting each point $P_i$ are acquired, a cardiac potential waveform is stationary, so that the RRIs are almost constant. As a result, each point $P_i$ is plotted in the vicinity of a straight line L0 which is a straight line of y=x, and the point group P is generated in the vicinity of the straight line L0. The distribution region of the point group P, that is, the distribution region of the respective points $P_i$ constituting the point group P, is formed in an elliptical shape and intersects the straight line L0. Here, the straight line L0 is a straight line indicating a state where each RRI constituting the RRI information is constant, on the xy plane.

(Description of Biological Signal Processing Device)

Figure 4:
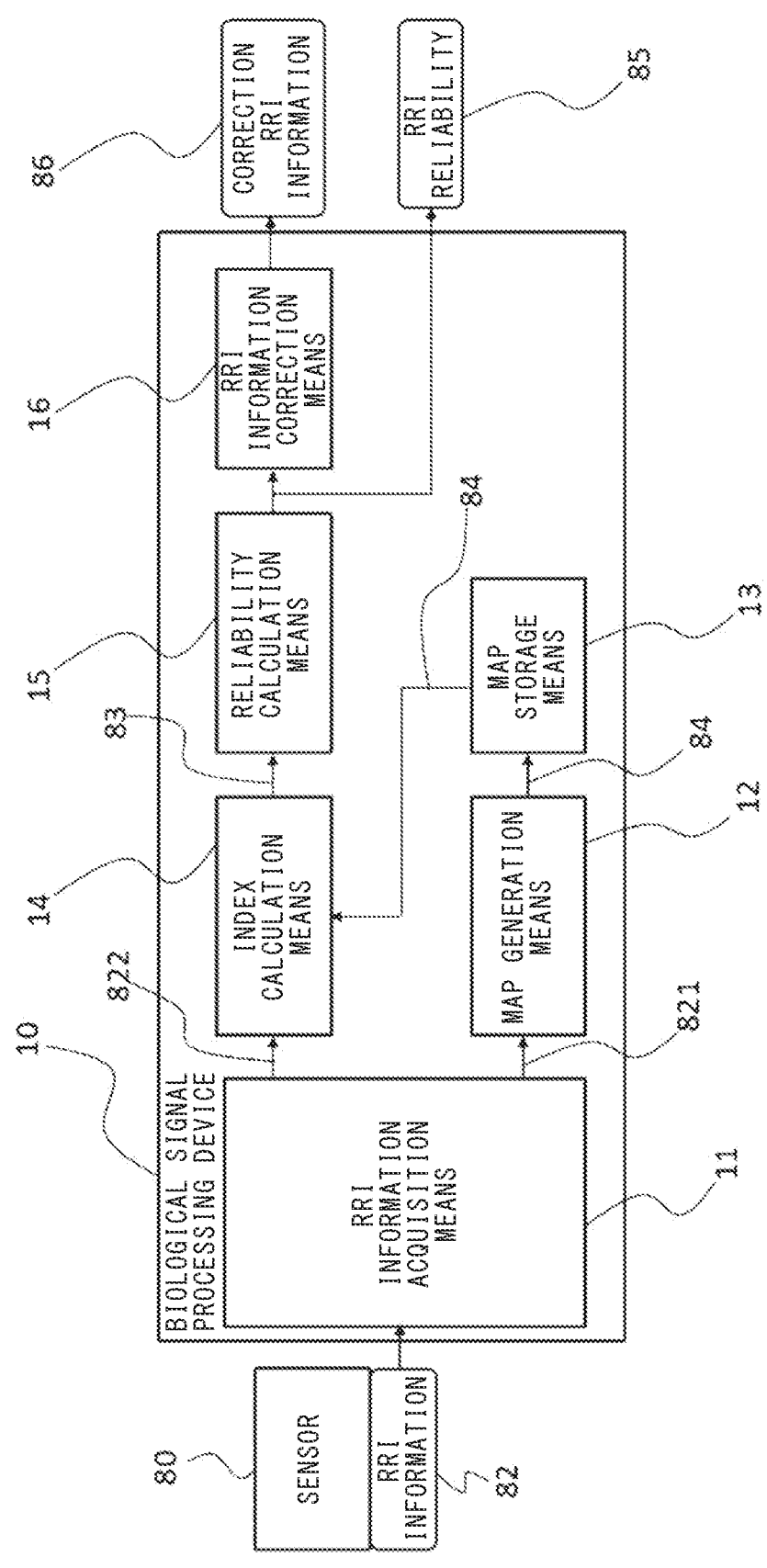
FIG. 4 is a block diagram showing a biological signal processing device according to Embodiment 1.

FIG. 4 is a block diagram showing a biological signal processing device according to Embodiment 1. A biological signal processing device 10 includes: an RRI information acquisition means 11 which acquires RRI information 82 outputted from a sensor 80; a map generation means 12 which generates a "map" for evaluating the reliability of the RRI information 82; a map storage means 13 which stores therein map information 84 of the map generated by the map generation means; an index calculation means 14 which calculates an index 83 of each RRI constituting the RRI information 82 to be evaluated, by using the map; a reliability calculation means 15 which calculates RRI reliability 85, which indicates the degree of reliability of each RRI constituting the RRI information 82 to be evaluated, from the index 83; and an RRI information correction means 16 which corrects the RRI information 82 on the basis of the RRI reliability 85 and outputs the corrected RRI information 82 as correction RRI information 86.

The sensor 80 calculates RRIs of a target to be watched, and outputs the RRI information 82 composed of the measured RRIs arranged in time series. In addition, when outputting the RRI information 82, the sensor 80 adds identification information (not shown) which identifies the target to be watched, to the RRI information 82. The identification information is also added to the RRI reliability 85 and the correction RRI information 86, which will be described later, and the RRI information 82, the RRI reliability 85, and the correction RRI information 86 are associated with the target to be watched. The sensor 80 may be any sensor that is capable of detecting a biological signal such as cardiac potential or a pulse wave and calculating an RRI from the detected biological signal. For example, a wearable sensor including an electrode that detects cardiac potential or an optical element that detects a pulse wave, or the like, can be used as the sensor 80. A non-contact type pulse wave sensor that detects a pulse wave from blood flow on the surface of a face can also be used.

The RRI information acquisition means 11 acquires the RRI information 82 periodically outputted from the sensor 80, during a predetermined period. The acquisition of the RRI information 82 in Embodiment 1 includes "acquisition in pre-learning" and "acquisition in actual operation" (described in detail later). The RRI information acquisition means 11 transmits RRI information 821 acquired through "acquisition in pre-learning", to the map generation means 12, and transmits RRI information 822 acquired through "acquisition in actual operation", to the index calculation means 14.

(Description of Map Generation Method)

The map generation means 12 generates a map from the RRI information 821 acquired in pre-learning. For the sake of description, the RRI information 821 is assumed to include M RRIs. That is, the RRI information 821 is information obtained by replacing N with M in equation (1). "M" is a predetermined number. The map generation means 12 plots M−1 points $P_i$ (i=1, 2, . . . M−1), that is, first points, on the xy plane according to equations obtained by replacing N with M in equation (2) and equation (3), to generate the point group P. The point group P generated thus intersects the straight line L0 (y=x) as shown in FIG. 3. In Embodiment 1, one in which the point group P is generated on the xy plane which is a feature space is defined as a "map". The "map" is used for evaluating the resemblance to heart rate variability of the RRI information 82 to evaluate the reliability of the RRI information 82. Therefore, the position of each point $P_i$ constituting the point group P for generating a map needs to be determined on the basis of the values of RRIs in a normal state. For this reason, when generating the point group P by pre-learning, the influence of data loss and noise is eliminated as much as possible to maintain the normal state. Specifically, pre-learning is performed with the sensor worn normally. In addition, while maintaining the above state, it is preferable to acquire as much RRI information 821 in various situations assumed during actual operation as possible, and generate a map. The map generation means 12 outputs information for reproducing the generated map, as the map information 84 to the map storage means 13. The map storage means 13 stores the map information 84 therein.

The map information 84 is information required for reproducing the map generated by the map generation means 12, in the feature space. In the case where a map is generated on the basis of the point group P as in Embodiment 1, the map information 84 includes the coordinates of all the points $P_i$ constituting the point group P. In Embodiment 1, as described above, the point group P is configured through pre-learning, and a map is generated on the basis of the point group P, so that the map is generated before the start of actual operation. Therefore, a process from later-described index calculation to RRI correction can be performed in real time in actual operation.

(Description of Index Calculation Method)

Figure 5:
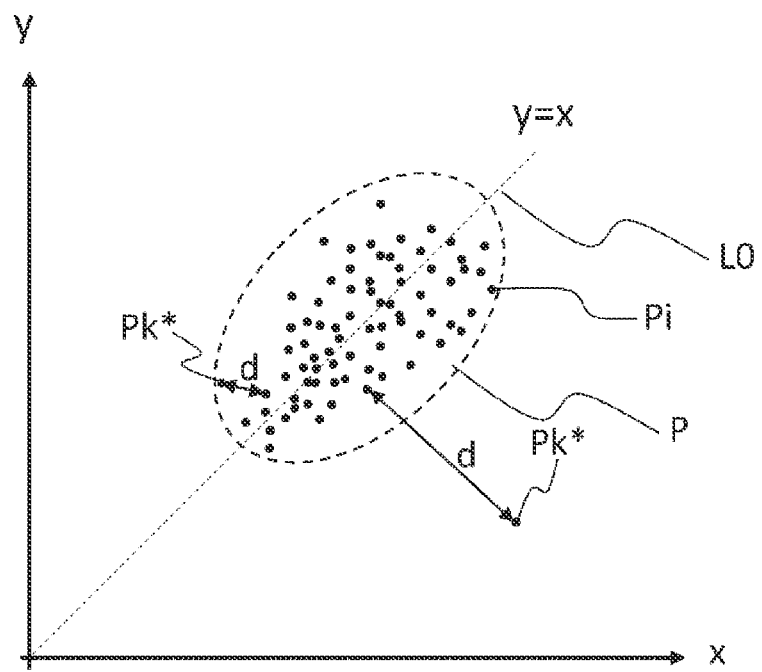
FIG. 5 illustrates an index calculation method according to Embodiment 1.

The index calculation means 14 calculates the index 83 of each RRI constituting the RRI information 822 to be evaluated that is acquired in actual operation. Here, the index 83 indicates the "resemblance to heart rate variability" of each RRI constituting the RRI information 822. FIG. 5 illustrates an index calculation method according to Embodiment 1. First, the index calculation means 14 acquires the map information 84 from the map storage means 13 and configures the point group P on the xy plane by using the map information 84, thereby reproducing the map. Next, the index calculation means 14 applies equation (2) to each RRI to be evaluated that constitutes the RRI information 822, and plots a point corresponding to the value of each RRI to be evaluated, on the xy plane. Here, it is assumed that N RRIs are acquired and the plotted points are points $P_k{}^*$ (k=1, 2, . . . N−1). The points $P_k{}^*$ correspond to second points. The index calculation means 14 calculates a degree of deviation of each point $P_k^*$ from the point group P as a value before calculating an index. As for a specific example of the "degree of deviation", it is considered that a smallest distance d between the point $P_k^*$ and the point $P_i$ among the distances between the point $P_k^*$ and the respective points $P_i$ constituting the point group P is defined as the degree of deviation of the point $P_k^*$. After the degree of deviation of each point $P_k^*$ is calculated, the index calculation means 14 calculates the index 83 of each RRI which is an element of the point $P_k^*$, from the degree of deviation of the point $P_k^*$. From equation (2), for example, an RRI(k) is an element of a point $P_{k-1}^*$ and also an element of the point $P_k^*$, so that each RRI may be elements of two points $P_k^*$. Therefore, it is considered that the simple average of the reciprocal of the degree of deviation of the point $P_{k-1}^*$ and the reciprocal of the degree of deviation of the point $P_k^*$ is defined as the index 83 of the RRI(k). Accordingly, the closer the point $P_k^*$ is to the point group P, the smaller the index 83 is and the larger the resemblance to heart rate variability is. After the index 83 of each RRI to be evaluated is calculated, the index calculation means 14 outputs the index 83 of each RRI to the reliability calculation means 15.

As for the degree of deviation of the point $P_k^*$, distances d of a plurality of points $P_i$ around the point $P_k^*$ may be calculated, and a predetermined number of (for example, 10) distances d from the smaller ones are added up to obtain a total value, and this total value may be used as the degree of deviation. In addition, the index 83 of each RRI is not limited to the simple average of the reciprocals of the degrees of deviation as described above, and may be the reciprocal of the sum of the degrees of deviation or may be the reciprocal of the maximum value or the minimum value among the degrees of deviation.

(Description of RRI Reliability Calculation)

For each RRI to be evaluated, the reliability calculation means 15 calculates the RRI reliability 85 on the basis of the index 83 of each RRI. The RRI reliability 85 is an index indicating the reliability of the measurement state of the biological signal, and is represented as a function of the index 83. That is, when the value of the index 83 of the RRI(k) is denoted by $\alpha(k)$ and the value of the RRI reliability 85 of the RRI(k) is denoted by $\beta(k)$, the following equation (4) is generally established.

$$\beta(k)=f(\alpha(k)) \tag{4}$$

Here, $\alpha(k)$ indicates the degree of resemblance to heart rate variability, and $\beta(k)$ indicates the reliability of the RRI(k), so that the function f is generally considered to be a monotonically increasing function. As a simplest form, the index 83 may be used as the RRI reliability 85 of the RRI. In addition, the function f is also considered to be a nonlinear monotonically increasing function such as a sigmoid function.

Moreover, the RRI reliability 85 may be calculated on the basis of the indexes 83 of the RRIs in certain previous and subsequent sections. That is, the RRI reliability 85 of the RRI(k) may be obtained by using the following equation (5).

$$\beta(k)=f(\alpha(k-j),\alpha(k-j+1) \ldots ,\alpha(k-1),\alpha(k),\alpha(k+1), \ldots \\ \alpha(k+j-1),\alpha(k+j)) \tag{5}$$

In equation (5), the RRI reliability 85 of the RRI(k) is obtained on the basis of the indexes 83 of the RRIs in a section [k−j, k+j]. More specifically, the average of the indexes 83 of the RRIs in the section [k−j, k+j] is considered to be the RRI reliability of the RRI(k).

The reliability calculation means 15 outputs the RRI reliability 85 of each RRI to the RRI information correction means 16. In addition, the reliability calculation means 15 outputs the RRI reliability 85 of each RRI as the output of the biological signal processing device 10 to a watching server 70 described later. The output of the RRI reliability 85 to the watching server 70 can be omitted in the case where later-described determination as to the worn state of the sensor 80 is not performed.

(Description of RRI Information Correction)

The RRI information correction means 16 compares the value of the RRI reliability 85 of each RRI with a predetermined threshold value th, and when the value of the RRI reliability 85 is smaller than the threshold value th, the RRI information correction means 16 invalidates the corresponding RRI. That is, the RRI information correction means 16 invalidates the RRI(k) in the case of $\beta(k)<$th. In addition, the RRI information correction means 16 corrects the RRI information 822, which is the RRI information to be evaluated, by deleting the invalidated RRI from the RRI information 822. The corrected RRI information 822 is outputted as the correction RRI information 86.

The biological signal processing device 10 of Embodiment 1 corrects the RRI information, but it is also considered that the biological signal processing device 10 performs up to calculation of the RRI reliability 85. In this case, the biological signal processing device 10 serves as a device for evaluating the reliability of the RRI information 82, and outputs the RRI reliability 85.

Moreover, considering that certain arrhythmias can occur even in normal conditions, only when the value of the RRI reliability 85 consecutively falls below the threshold value th a predetermined number of times, the corresponding RRI may be invalidated. For example, in the case where the above predetermined number of times is set to 2, if $\beta(k-1)$ <th and $\beta(k)$, or if $\beta(k)<$th and $\beta(k+1)$, the RRI(k) may be invalidated. Accordingly, RRIs in arrhythmias that can occur in normal conditions can be left in the correction RRI information 86, and accidental deletion of normal RRIs can be prevented.

(Description of Hardware Configuration)

Next, the hardware configuration for implementing the function units of the biological signal processing device 10 will be described.

Figure 6:
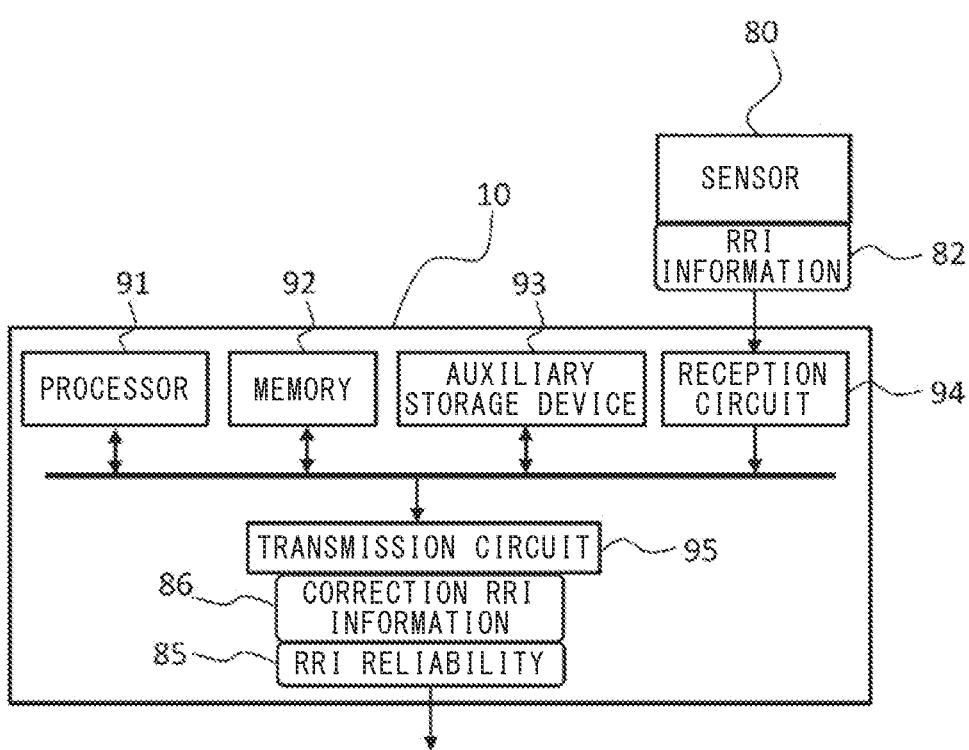
FIG. 6 illustrates an example of the hardware configuration of the biological signal processing device according to Embodiment 1.

FIG. 6 illustrates an example of the hardware configuration for implementing the function units of the biological signal processing device 10. The biological signal processing device 10 is composed mainly of a processor 91, a memory 92 as a main storage device, and an auxiliary storage device 93. The processor 91 is composed of, for example, a central processing unit (CPU), an application specific integrated circuit (ASIC), a digital signal processor (DSP), a field programmable gate array (FPGA), or the like. The memory 92 is composed of a volatile storage device such as a random access memory, and the auxiliary storage device 93 is composed of a nonvolatile storage device such as a flash memory, a hard disk, or the like. In the auxiliary storage device 93, a predetermined program to be executed by the processor 91 is stored. The processor 91 reads and executes this program as appropriate to perform various arithmetic processes. At this time, the predetermined program is temporarily stored in the memory 92 from the auxiliary storage device 93, and the processor 91 reads this program from the memory 92. The arithmetic processes by the function units shown in FIG. 4 are realized by the processor 91 executing the predetermined program as described above. The results of the arithmetic processes by the processor 91 are stored in the memory 92 once, and are stored in the auxiliary storage device 93 according to the purposes of the executed arithmetic processes.

Moreover, the biological signal processing device 10 includes a reception circuit 94 which receives the RRI information 82 outputted by the sensor 80, and a transmission circuit 95 which transmits the RRI reliability 85 and the correction RRI information 86 outputted by the biological signal processing device 10, to an external device.

(Description of Watching System)

Figure 7A:
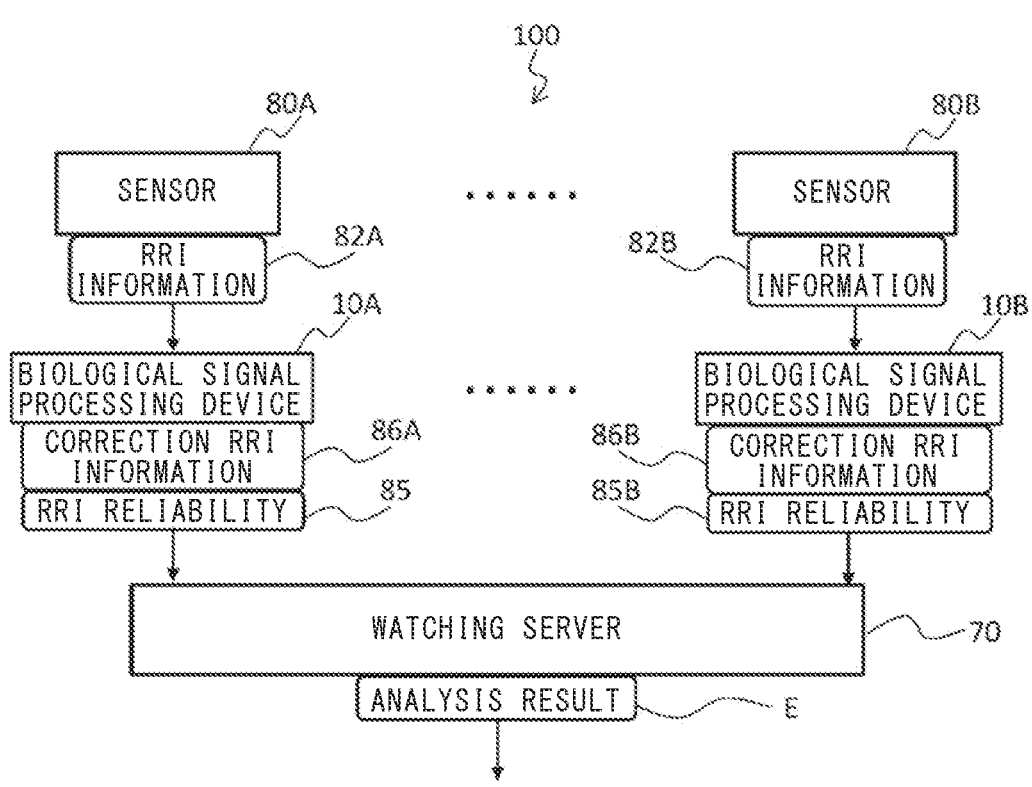
FIG. 7A is a block diagram showing a watching system according to Embodiment 1.
Figure 7B:
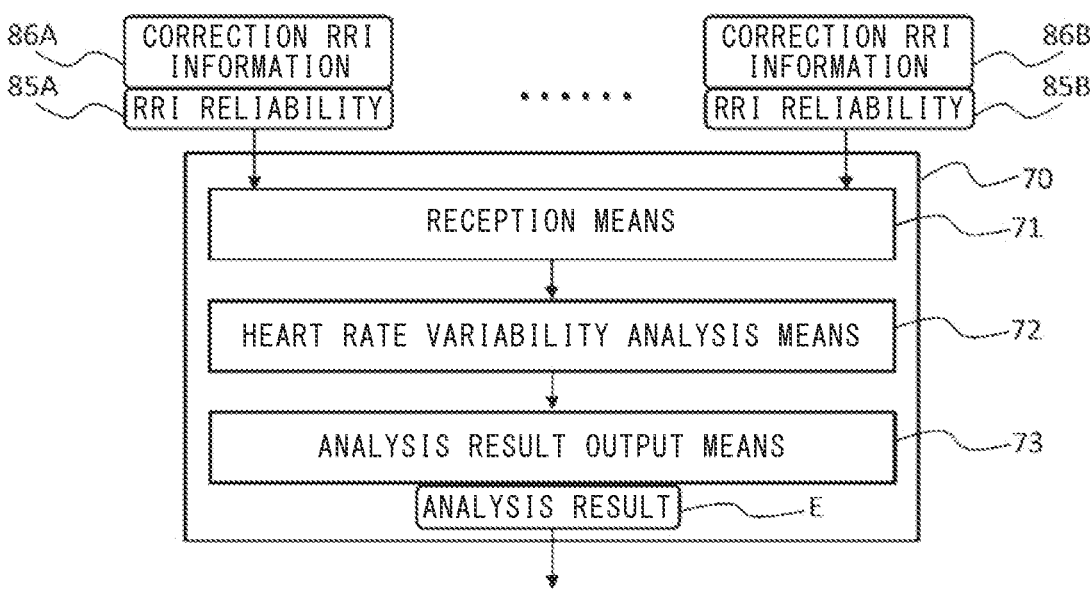
FIG. 7B is a block diagram showing a watching server according to Embodiment 1.

FIG. 7A is a block diagram showing a watching system according to Embodiment 1, and FIG. 7B is a block diagram showing a watching server according to Embodiment 1. A watching system 100 includes: sensors 80A and 80B each of which detects a biological signal of a target to be watched, such as cardiac potential or a pulse wave, sequentially calculates RRIs of the detected biological signal, and outputs RRI information 82A or 82B composed of a plurality of the RRIs arranged in time series; biological signal processing devices 10A and 10B which correspond to the sensors 80A and 80B, respectively, and each of which processes the RRI information 82A or 82B outputted by the sensor 80A or 80B to generate RRI reliability 85A or 85B and correction RRI information 86A or 86B; and the watching server 70 which receives the RRI reliability 85 and the correction RRI information 86 outputted by each of the biological signal processing devices 10A and 10B, analyzes the correction RRI information 86, and outputs an analysis result E. The configurations of the biological signal processing devices 10A and 10B are the same as that of the biological signal processing device 10 described with reference to FIG. 4. That is, a map is generated from the RRIs constituting the RRI information 82A or 82B acquired from the sensor 80A or the sensor 80B, the index 83 indicating the resemblance to heart rate variability of each RRI to be evaluated is calculated, and the reliability of each RRI is calculated by using the index 83, thereby obtaining the RRI reliability 85A or 85B. In addition, the RRI information 82A or 82B is corrected by the RRI reliability 85A or 85B to obtain the correction RRI information 86A or 86B. The specific description of the map generation, the calculation of the index 83, the calculation of the RRI reliability, and the correction of the RRI information 82 is as described above.

(Description of Watching Server)

The watching server 70 includes: a reception means 71 which receives the RRI reliability 85A and 85B and the correction RRI information 86A and 86B; a heart rate variability analysis means 72 which analyzes the heart rate variability of targets to be watched on the basis of the correction RRI information 86A and 86B, respectively, and estimates the physical loads, the states of the autonomic nerves, and the like of the targets to be watched; and an analysis result output means 73 which outputs a result of the analysis by the heart rate variability analysis means 72, as the analysis result E.

(Description of Heart Rate Variability Analysis)

The heart rate variability analysis means 72 analyzes the heart rate variability of each target to be watched from the time-series variation of each RRI constituting the correction RRI information 86A or 86B. For example, the activation balance between the parasympathetic nerves and the sympathetic nerves may be evaluated from the intensity distribution of respiratory arrhythmia components to estimate the state of the autonomic nerves, thereby evaluating the intensity of stress on the target to be watched. In addition, the variation of work load or exercise load and the variation of the RRIs are compared with each other, and the physical load of the target to be watched is estimated. Specifically, the physical load of the target to be watched is estimated from the variation of the RRIs with respect to the variation of work load or the like (the heart rate increases when the work load or the like increases, and the heart rate also returns when the work load or the like returns to normal). The variation of work load or the like can be grasped, for example, by measuring the movement of the target to be watched with an acceleration sensor or the like and determining whether there is any deviation in the measured acceleration. The heart rate variability analysis means 72 outputs the analysis result E to the analysis result output means 73.

As described above, in Embodiment 1, the RRIs whose RRI reliability values are smaller than the threshold value th are invalidated and are not included in the correction RRI information 86A and 86B. Therefore, the above-described analysis of heart rate variability can be performed in a state where the influence of an abnormality in wearing of the sensors 80A and 80B is eliminated.

Prior to analysis of heart rate variability, the heart rate variability analysis means 72 may determine whether there is an abnormality in the worn state of the sensor 80A or 80B worn by the target to be watched. Specifically, for each RRI constituting the received correction RRI information 86A or 86B, if a state where the value of the RRI reliability falls below the threshold value th continues for a predetermined period, the heart rate variability analysis means 72 determines that there is an abnormality in the worn state of the sensor 80A or 80B. In such a case, the heart rate variability analysis means 72 adds a warning message indicating the wearing abnormality, to the analysis result E.

The analysis result output means 73 outputs the analysis result E to an external display device or the like to display the contents of the analysis result E to a supervisor or the like.

In the example shown in FIG. 7A, one biological signal processing device corresponds to one sensor, but one biological signal processing device may correspond to a plurality of sensors. In this case, the biological signal processing device processes RRI information outputted by each of the corresponding sensors, and outputs RRI reliability and correction RRI information for each RRI information.

(Description of Watching Method)

Figure 8:
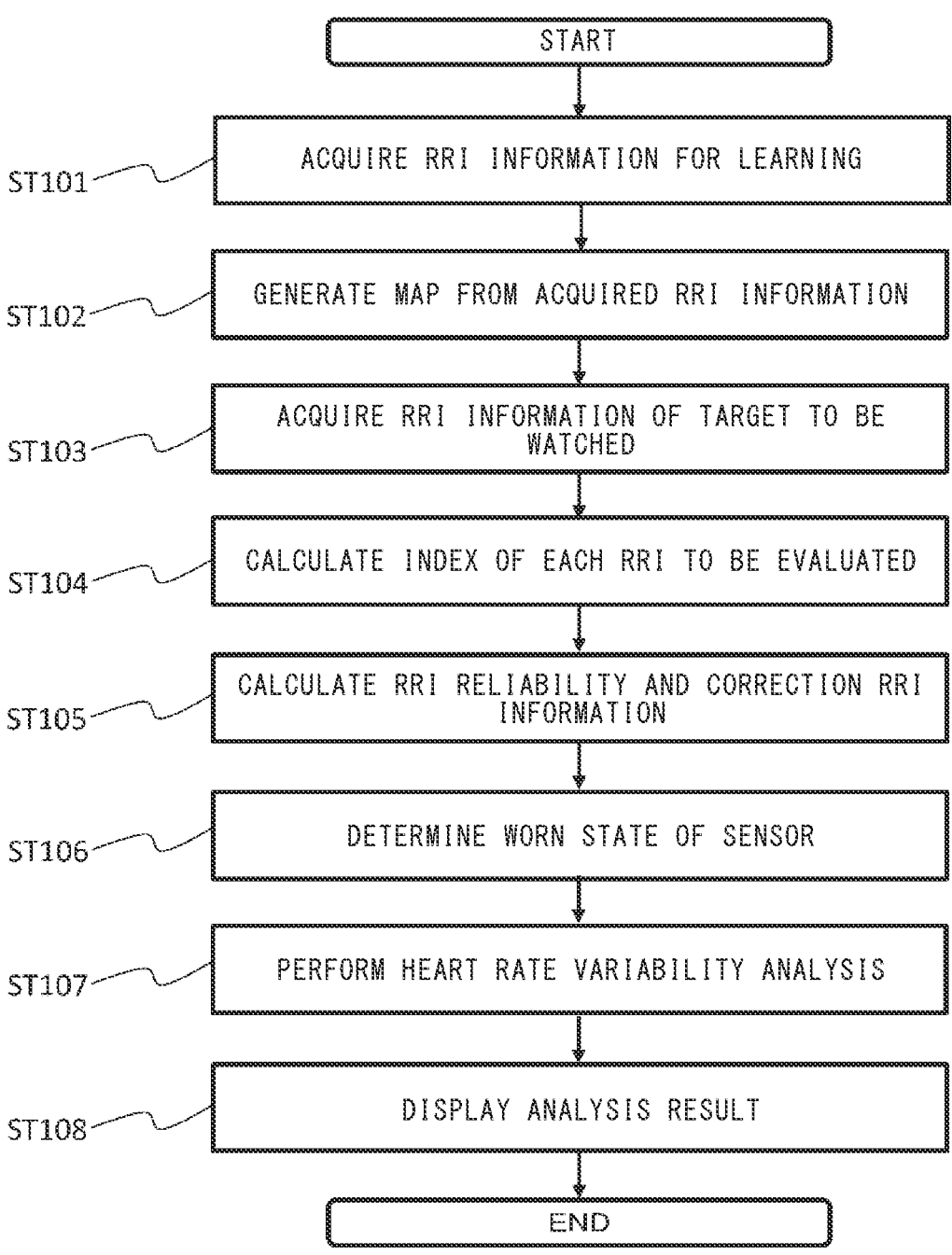
FIG. 8 is a flowchart showing the operation of the watching system according to Embodiment 1.

Next, operation will be described. FIG. 8 is a flowchart showing the operation of the watching system according to Embodiment 1, that is, a watching method according to Embodiment 1. In FIG. 8, step ST101 and step ST102 are a pre-learning process, and step ST103 to step ST108 are an actual operation process. First, RRI information for learning is acquired (step ST101). The sensors 80A and 80B each detect a biological signal, in normal conditions, of the target to be watched, and calculate RRIs of the detected biological signal in time series. The RRI information acquisition means 11 of the biological signal processing devices 10A and 10B each acquire the RRI information 82A or 82B composed of a plurality of the RRIs arranged in time series, from the sensor 80A or 80B.

Next, a map is generated from the RRI information in normal conditions acquired in step ST101 (step ST102). The map generation means 12 of the biological signal processing devices 10A and 10B each configure a point group P as a map on the xy plane by using the RRI information 821. Specific generation of the point group P is as described above. The map generation means 12 stores the coordinates of all points $P_i$ constituting the point group P, as the map information 84 in the map storage means 13. Thus, the pre-learning process is completed.

Next, RRI information of the target to be watched is acquired in actual operation (step ST103). The RRI information acquisition means 11 of the biological signal processing devices 10A and 10B acquires the RRI information 82A and 82B periodically outputted from the sensors 80A and 80B which detect biological signals of the targets to be watched. The RRI information 82A and 82B acquired by the biological signal processing devices 10A and 10B, respectively, are outputted as the RRI information 822 to be evaluated, to the index calculation means 14 of the biological signal processing devices 10A and 10B.

Next, the index of each RRI to be evaluated is calculated (step ST104). As described above, the index calculation means 14 of the biological signal processing devices 10A and 10B each calculate the index 83 of each RRI from the degree of deviation between the point $P_k^*$ corresponding to each RRI to be evaluated that constitutes the RRI information 822 and the point group P generated in pre-learning.

Next, RRI reliability and correction RRI information are calculated (step ST105). The reliability calculation means 15 of the biological signal processing devices 10A and 10B calculates the RRI reliability 85A and 85B from the index 83 of each RRI calculated in step ST104, and outputs the RRI reliability 85A and 85B to the RRI information correction means 16 of the biological signal processing devices 10A and 10B and the watching server 70. The RRI information correction means 16 of the biological signal processing devices 10A and 10B corrects the RRI information 822 to be evaluated, on the basis of the RRI reliability 85A and 85B to obtain the correction RRI information 86A and 86B. A specific method for correcting the RRI information is as described above. The RRI information correction means 16 of the biological signal processing devices 10A and 10B outputs the correction RRI information 86A and 86B to the watching server 70.

Next, the worn state of the sensor 80 is determined (step ST106). The watching server 70 receives the RRI reliability 85A and 85B and the correction RRI information 86A and 86B outputted from the biological signal processing devices 10A and 10B, by the reception means 71, and the heart rate variability analysis means 72 of the watching server 70 compares the values of the RRI reliability 85A and 85B with the threshold value th, thereby determining the worn states of the sensors 80A and 80B, respectively.

Next, the heart rate variability of the target to be watched is analyzed (step ST107). The heart rate variability analysis means 72 estimates the states of the autonomic nerves and the physical loads of the targets to be watched, from the time-series variation of the RRIs constituting the correction RRI information 86A and 86B. A specific analysis method is as described above.

Next, the analysis result is displayed (step ST108). The analysis result output means 73 of the watching server 70 outputs the analysis result E by the heart rate variability analysis means 72, to an external display device or the like to display the contents of the analysis result E to a supervisor or the like. At this time, if there is information to warn the supervisor of, display of a warning message, output of a warning sound, or the like is performed. The supervisor performs confirmation of the worn state of the sensor on the target to be watched, confirmation of the safety of the target to be watched, or the like, according to the contents of the analysis result E and the warning.

Figure 9A:
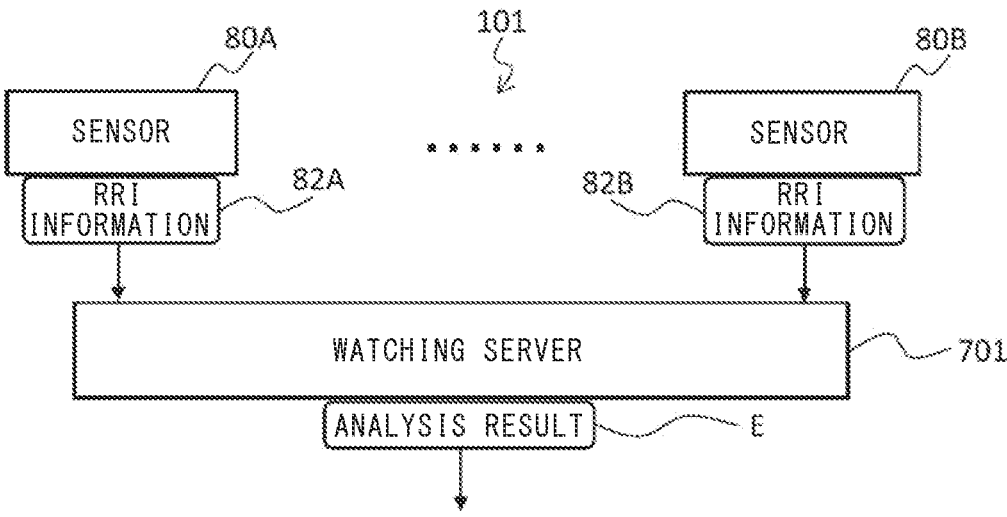
FIG. 9A is a block diagram showing a watching system according to another example of Embodiment 1.
Figure 9B:
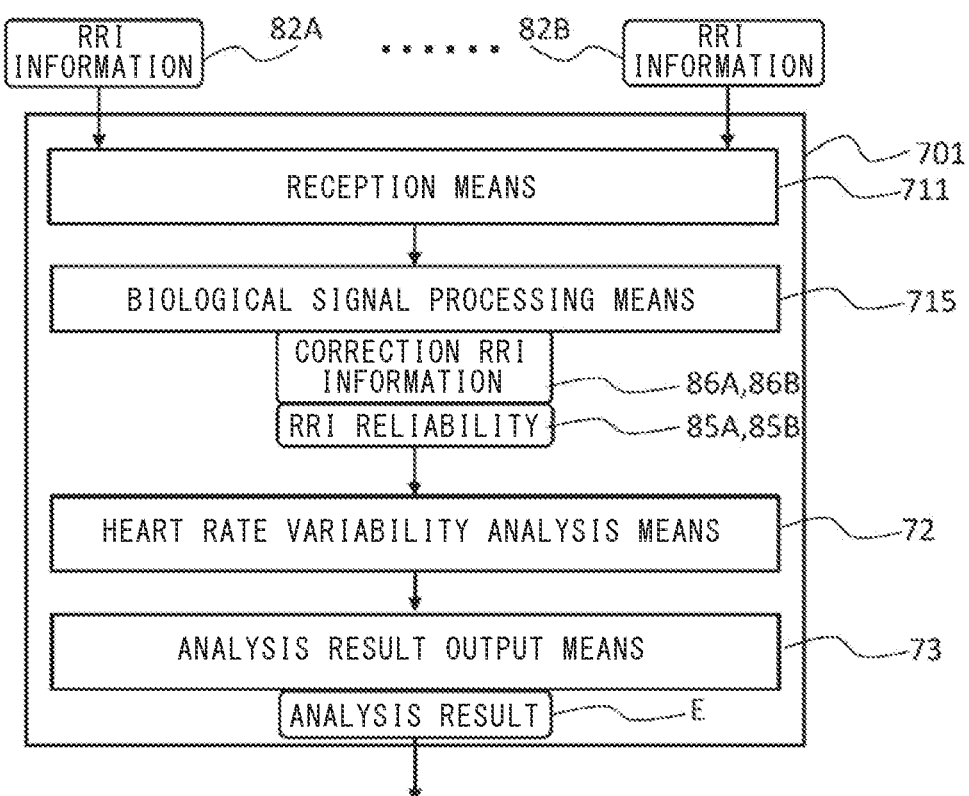
FIG. 9B is a block diagram showing a watching server according to another example of Embodiment 1.

Next, another example of the watching system according to Embodiment 1 will be described. FIG. 9A is a block diagram showing a watching system according to another example of Embodiment 1, and FIG. 9B is a block diagram showing a watching server according to the other example of Embodiment 1. A watching system 101 includes: sensors

80A and 80B each of which detects a biological signal of a target to be watched, calculates RRIs of the detected biological signal in time series, and outputs RRI information 82A or 82B composed of a plurality of the RRIs arranged in time series; and a watching server 701 which acquires the RRI information 82A and 82B outputted by the sensors 80A and 80B, and outputs a result obtained by analyzing the acquired RRI information 82A and 82B, as an analysis result E.

The watching server 701 includes: a reception means 711 which receives the RRI information 82A and 82B; a biological signal processing means 715 which generates RRI reliability 85A and 85B and correction RRI information 86A and 86B from the RRI information 82A and 82B; a heart rate variability analysis means 72 which analyzes the heart rate variability of targets to be watched on the basis of the correction RRI information 86A and 86B, respectively, and estimates the physical loads, the states of the autonomic nerves, and the like of the targets to be watched; and an analysis result output means 73 which outputs a result of the analysis by the heart rate variability analysis means 72, as an analysis result E. The configuration of the biological signal processing means 715 is the same as that of the biological signal processing device 10. In addition, the other configuration is also the same as that of the watching server 70. As described above, the watching server 701 is configured by incorporating the function of the biological signal processing device 10 into the watching server 70, to directly acquire the RRI information 82A and 82B from the sensors 80A and 80B and perform correction of RRI information, etc., within the watching server.

As can be seen by comparing the watching system 100 and the watching system 101, it is possible to transfer some functions of the biological signal processing device 10 to the watching server 70. In short, it is sufficient that in the watching system 100, acquisition of RRI information, correction of the RRI information, analysis of heart rate variability, and output of an analysis result can be performed. For example, it is also considered that the heart rate variability analysis means 72 is provided in the biological signal processing device 10. In this case, offline analysis of heart rate variability is possible, and the analysis result E is transmitted from the biological signal processing device 10 to the watching server 70. The watching server 70 merely performs display of the analysis result E to a supervisor, etc.

Moreover, although not shown, it is also considered that a map storage means which stores therein map information and a transmission means which transmits the map information are provided in the watching server 70, a map generated by the biological signal processing device 10A is stored in the map storage means of the watching server, and the map is shared by the biological signal processing devices 10A and 10B. In this case, the pre-learning process can be omitted if map information of an available map is already stored in the watching server 70.

In Embodiment 1, a two-dimensional plane is used as the feature space, but the feature space may be a three or more dimensional space. In the case where the feature space is three-dimensional, the coordinates of each point $P_i$ constituting the point group P is composed of three adjacent RRIs (for example, $P_i=(RRI(i-1), RRI(i), RRI(i+1))^T$). In the case where the feature space is an xyz space, if RRIs are stationary, the points $P_i$ constituting the point group P are distributed in the vicinity of a straight line x=y=z, so that the index 83 and the RRI reliability 85 of each RRI can be calculated in the same manner as in the case where the feature space is two-dimensional.

The biological signal processing device of Embodiment 1 can evaluate the reliability of the measurement state of the biological signal on the basis of the RRI information. More specifically, the biological signal processing device includes: the map generation means which generates a map from the feature space by plotting a plurality of points whose positions are determined on the basis of the values of the RRIs in the normal state among the RRIs of the biological signal of the target to be watched, on the feature space; the index calculation means which calculates an index indicating the resemblance to heart rate variability of each RRI to be evaluated, by comparing each point whose position is determined on the basis of the value of the RRI to be evaluated, with the map; and the reliability calculation means which calculates RRI reliability indicating the reliability of each RRI to be evaluated, from the index. Accordingly, a map serving as a basis for evaluation is generated in pre-learning, and the reliability of the value of each measured RRI of the target to be watched is evaluated from only the RRI information in actual operation. Therefore, for the target to be watched, the reliability of the measurement state of the biological signal can be evaluated on the basis of the RRI information.

Moreover, since the RRI information correction means which corrects the RRI information by deleting the RRI whose RRI reliability falls below the predetermined threshold value, from the RRI information, is included, the influence of a wearing abnormality on heart rate variability analysis can be suppressed.

Moreover, the watching system of Embodiment 1 can evaluate the reliability of the measurement state of the biological signal on the basis of the RRI information, and grasp the state of the target to be watched from the RRI information. More specifically, the watching system includes: the sensor which calculates RRIs of the biological signal of the target to be watched; the biological signal processing device of Embodiment 1 which acquires the RRI information from the corresponding sensor; and the watching server including the heart rate variability analysis means which analyzes the heart rate variability of the target to be watched, on the basis of the correction RRI information received from the signal processing device of Embodiment 1. The biological signal processing device of Embodiment 1 can evaluate the reliability of the measurement state of the biological signal on the basis of the RRI information as described above. Furthermore, analysis of heart rate variability can be performed on the basis of the RRI information by the heart rate variability analysis means in the watching server, so that the state of the target to be watched can be grasped from the RRI information.

Moreover, the heart rate variability analysis means evaluates the worn state of the sensor on the basis of the RRI reliability, so that a warning indicating an abnormality in wearing of the sensor can be issued to the supervisor.

Embodiment 2

Figure 10:
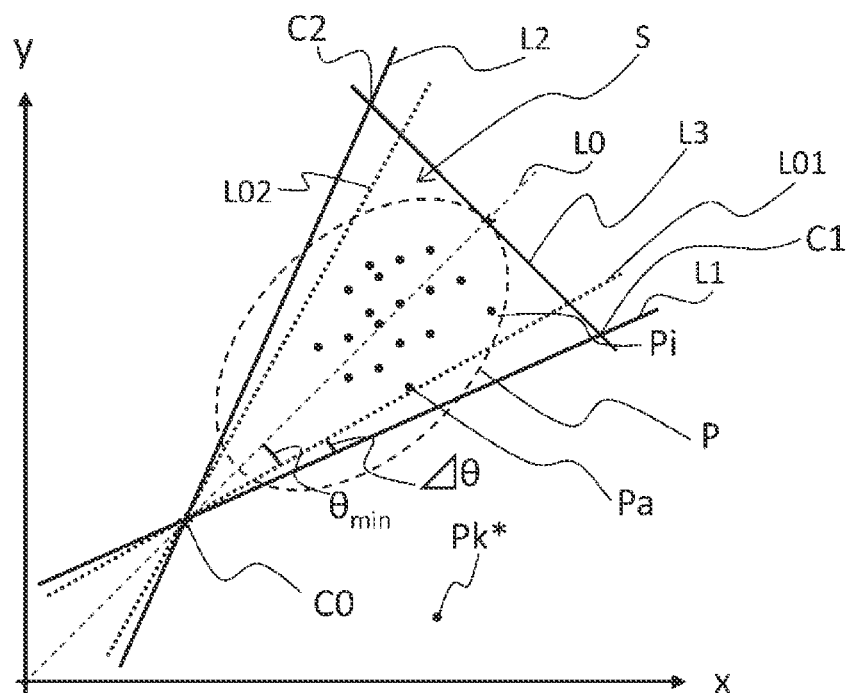
FIG. 10 illustrates a map and an index calculation method according to Embodiment 2.

Next, Embodiment 2 will be described with reference to FIG. 10. Embodiment 2 is different from Embodiment 1 in a method for generating a map for evaluating the reliability of RRI information and a method for calculating the index of an RRI. FIG. 10 illustrates a map and an index calculation method according to Embodiment 2. In Embodiment 2, a region determined so as to include a point group obtained in pre-learning is set as a normal region, and in actual operation, on the basis of whether a point plotted by using each RRI to be evaluated is within the normal region or outside the normal region, an index of the RRI is determined. Hereinafter, a detailed description will be given.

(Description of Map Generation Method)

First, the map generation means 12 configures a point group P from the RRI information 821 acquired for pre-learning. As for the generation of the point group P, similar to Embodiment 1, equation (2) and equation (3) may be applied to, for example, M RRIs. Similar to Embodiment 1, the point group P intersects a straight line L0, and the distribution range of points $P_i$ is formed in an elliptical shape.

Next, a straight line L01 which passes through a point Pa located farthest from a straight line L0 (y=x) among the points $P_i$ constituting the point group P and which intersects the straight line L0 at an intersection point C0, is drawn. Here, it is assumed that an angle between the straight line L0 and the straight line L01 is θmin. Next, an angle θ (=θmin+Δθ) obtained by adding a margin Δθ to θmin is calculated, and a straight line L1 which intersects the straight line L0 at the intersection point C0 and whose angle with respect to the straight line L0 is θ, is drawn. Furthermore, a straight line L2 which is symmetrical with the straight line L1 about the straight line L0 as an axis of symmetry, is drawn. In addition, a straight line L3 which has a gradient of −1 and which intersects the straight line L1 and the straight line L2 at an intersection point C1 and an intersection point C2, respectively, is drawn. A region surrounded by the straight line L1, the straight line L2, and the straight line L3 is set as a normal region S. A straight line L02 in the drawing is a straight line that is symmetrical with the straight line L01 about the straight line L0 as an axis of symmetry. Therefore, an angle between the straight line L02 and the straight line L0 is also θmin (note that the angle is not shown in FIG. 10).

Since θmin is the minimum angle for including all the points $P_i$ constituting the point group P, all the points $P_i$ constituting the point group P are included in the region surrounded by the straight line L01, the straight line L02, and the straight line L3. Since the angles of the straight line L1 and the straight line L2 with respect to the straight line L0 are larger by the margin Δθ than those of the straight line L01 and the straight line L02, all the points $P_i$ constituting the point group P are also included in the normal region S which is the region surrounded by the straight line L1, the straight line L2, and the straight line L3. In Embodiment 2, one in which the normal region S is set on an xy plane which is a feature space is defined as a "map". Since the normal region S is determined by the straight lines L1, L2, and L3, the map information 84 in Embodiment 2 may include mathematical formulas indicating the straight lines L1, L2, and L3, which are the boundary of the normal region S, or coefficients determining the mathematical formulas, etc. Therefore, it is not necessary to include coordinate information of all the points $P_i$ constituting the point group P, in the map information 84 as in Embodiment 1.

The positions of the intersection points C0, C1, and C2 are determined in advance. It is considered that, on the basis of the physiological findings, the positions of the intersection points C1 and C2 are determined from the possible maximum heartbeat interval value, and the position of the intersection point C0 is determined from the possible minimum heartbeat interval value. In the generation of a map in Embodiment 1, it is necessary to increase the number of samples in pre-learning, and to configure a point group P after more exhaustive sampling. In Embodiment 2, the range of the map can be adjusted by setting the intersection points on the basis of the physiological findings, so that the map can be adjusted more flexibly than in Embodiment 1. Thus, for example, even if only data in a state where the instantaneous heart rate is low is obtained in pre-learning, a map that also assumes a state where the instantaneous heart rate is high can be generated.

Moreover, the normal region S shown in FIG. 10 is an isosceles triangle that has a vertex angle at the intersection point C0 and whose base is a line segment connecting the intersection point C1 and the intersection point C2. However, the normal region S may be any region including all the points $P_i$ constituting the point group P on the boundary thereof or therein, and the geometric shape of the normal region S is not particularly limited. For example, an ellipse or a diamond shape may be used. In addition, it is considered that a cone that includes all the points $P_i$ constituting a point group P in the case where the feature space is a three-dimensional xyz space, on the boundary thereof or therein and that intersects a straight line x=y=z at the vertex and the bottom surface center thereof, is used as the normal region S.

(Description of Index Calculation Method)

The index calculation means 14 calculates the index 83 of each RRI constituting the RRI information 822 to be evaluated that is acquired in actual operation. First, the index calculation means 14 acquires the map information 84 from the map storage means 13, and sets the normal region S on the xy plane by using the map information 84, thereby reproducing the map. Next, the index calculation means 14 applies equation (2) to each RRI to be evaluated that constitutes the RRI information 822, and plots a point corresponding to the value of each RRI to be evaluated, on the xy plane. The index calculation means 14 determines whether or not each point $P_k^*$ is within the normal region S, assigns "1" to the points $P_k^*$ that are within the normal region S, and assigns "0" to the points $P_k^*$ that are outside the normal region S. After "0" or "1" is assigned to all the points $P_k^*$ as described above, the indexes 83 of the RRIs constituting each point $P_k^*$ are calculated in the same manner as in Embodiment 1. That is, the equivalent of a degree of deviation 831 of each point $P_k^*$ described in Embodiment 1 may be considered to be "0" or "1". The index calculation means 14 outputs the index 83 of each RRI to the reliability calculation means 15.

The others are the same as in Embodiment 1, and thus the description thereof is omitted.

In Embodiment 2, "0" or "1" is assigned to the points $P_k^*$ in index calculation, and the numerical value to be assigned to each point $P_k^*$ is determined by the position of the point $P_k^*$. That is, the numerical value indicating the "resemblance to heart rate variability" is determined by a position on the xy plane. Using this fact, potential information in which "1" is set for the inside of the normal region S and "0" is set for the outside of the normal region S is set in map generation, and one obtained by adding the potential information to the feature space may be used as a map. In this case, the map information 84 includes the above potential information. In addition, in index calculation, a value of "0" or "1" may be assigned to each point $P_k^*$ according to the position of the point $P_k^*$ and the above potential information.

According to Embodiment 2, the same advantageous effects as those of Embodiment 1 can be achieved.

Moreover, a map is generated by setting a normal region on the feature space. Therefore, the map information may include a mathematical formula indicating the boundary of the normal region or a coefficient determining the mathematical formula, so that the information amount of the map information can be reduced.

Embodiment 3

Figure 11:
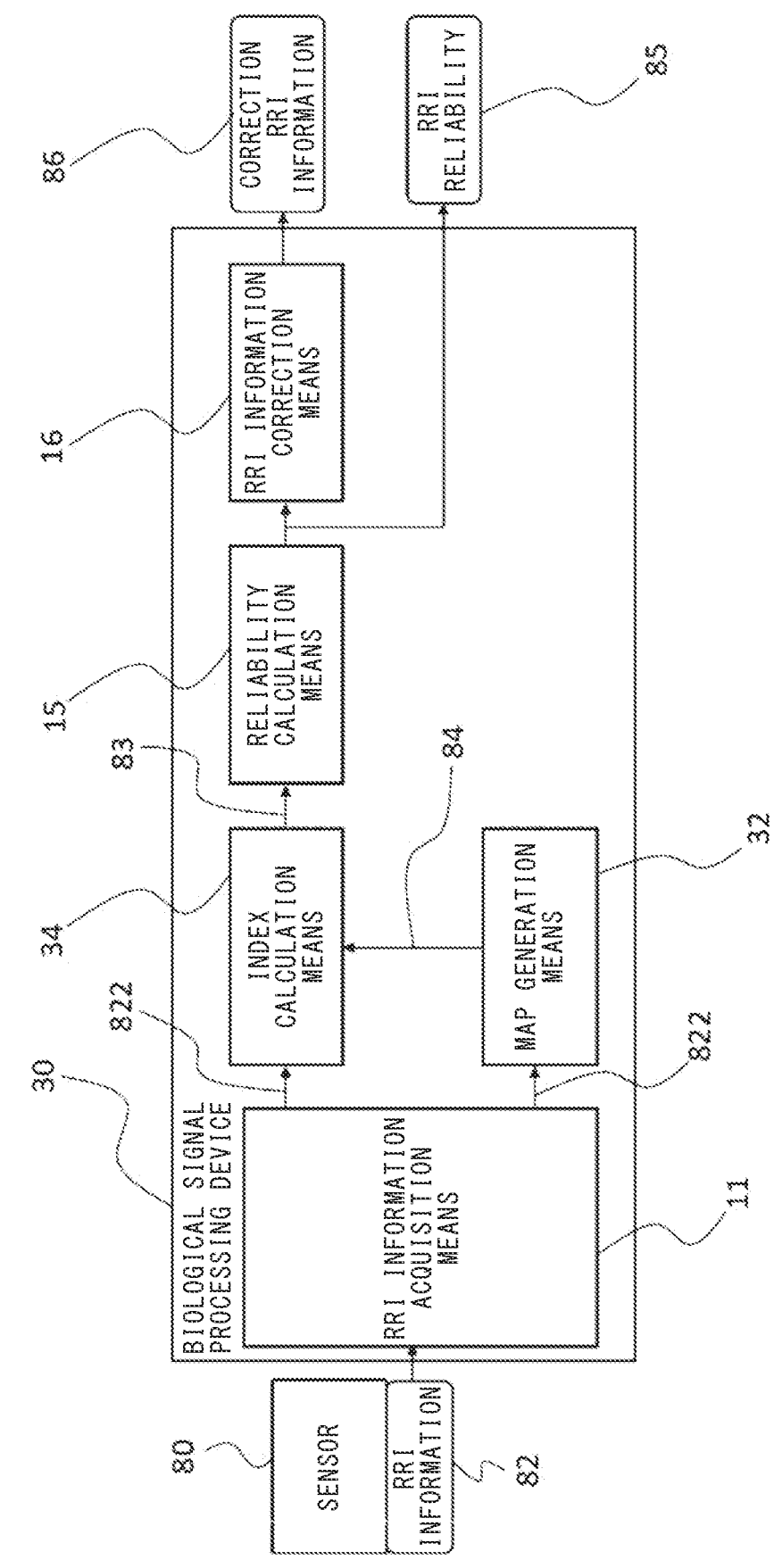
FIG. 11 is a block diagram showing a biological signal processing device according to Embodiment 3.
Figure 12:
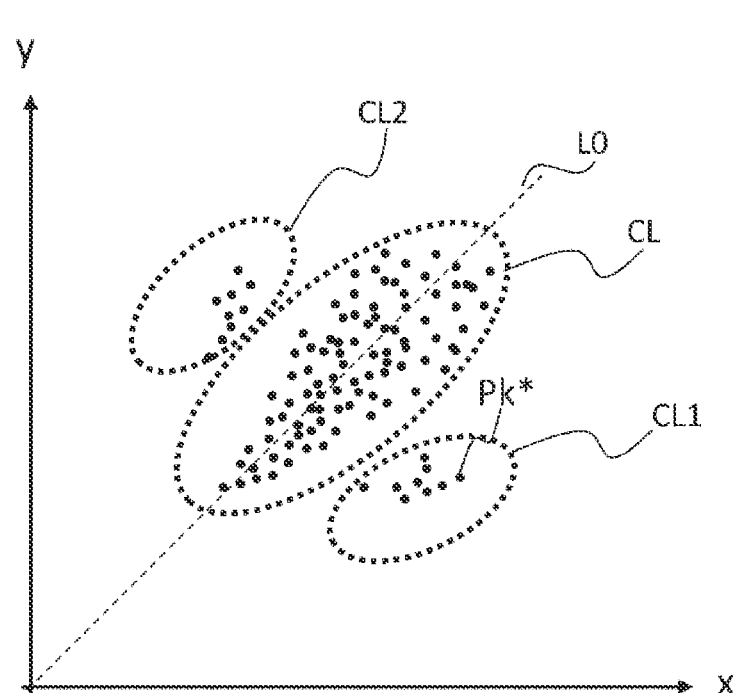
FIG. 12 illustrates a map and an index calculation method according to Embodiment 3.

Next, Embodiment 3 will be described with reference to FIG. 11 to FIG. 13. Embodiment 3 is different from Embodiment 1 and Embodiment 2 in that a map is generated by using RRI information acquired not in pre-learning but in actual operation. FIG. 11 is a block diagram showing a biological signal processing device according to Embodiment 3, and FIG. 12 illustrates a map and an index calculation method according to Embodiment 3. As shown in FIG. 11, the RRI information acquisition means 11 of a biological signal processing device 30 outputs the RRI information 822 acquired through "acquisition in actual operation" to both an index calculation means 34 and a map generation means 32. The index calculation means 34 calculates the index 83 of the RRI information 822 by using a map. In addition, in Embodiment 3, a map storage means is not essential, and thus the biological signal processing device 30 does not include a map storage means. Hereinafter, a detailed description will be given.

(Description of Map Generation Method)

The map generation means 32 determines the coordinates of the points $P_k^*$ from the RRIs constituting the RRI information 822 acquired in actual operation, according to equation (2), plots each point $P_k^*$ on the xy plane, and classifies each point $P_k^*$ by a clustering method such as a self-organizing map or k-means method, to form a plurality of point groups. In Embodiment 3, these point groups are referred to as "clusters". In the example shown in FIG. 12, three clusters (clusters CL, CL1, and CL2) are formed. Next, among the formed clusters, a cluster that intersects a straight line L0 is set as a valid cluster, and a cluster that does not intersect the straight line L0 is set as an invalid cluster. In the example shown in FIG. 12, the cluster CL is a valid cluster, and the clusters CL1 and CL2 are invalid clusters. In Embodiment 3, one in which the valid cluster and the invalid clusters are generated on the xy plane which is a feature space is defined as a "map". The map information 84 of Embodiment 3 may include the coordinates of each point $P_k^*$ included in the cluster CL which is a valid cluster. This is because the points $P_k^*$ that are not included in the cluster CL which is a valid cluster are included in the invalid clusters. The map generation means 32 outputs the map information 84 to the index calculation means 34.

(Description of Index Calculation Method)

The index calculation means 34 assigns "1" to the points $P_k^*$ included in the valid cluster, and assigns "0" to the other points $P_k^*$, that is, the points $P_k^*$ included in the invalid clusters, in the map reproduced by using the map information 84. Then, the index calculation means 34 calculates the indexes 83 of the RRIs constituting each point $P_k^*$, in the same manner as in Embodiment 1. The index calculation means 34 outputs the index 83 of each RRI to the reliability calculation means 15.

Since the RRIs that determine the coordinates of each point $P_k^*$ are the RRIs acquired in actual operation, there is a possibility that an abnormal value is also included. In Embodiment 3, the points $P_k^*$ included in the valid cluster are regarded as valid and "1" is assigned thereto, and the points $P_k^*$ included in the invalid clusters are regarded as invalid and "0" is assigned thereto, so that the discrimination of whether each RRI is normal or abnormal is reflected in the index 83 calculated therefrom.

The process after the index calculation is the same as in Embodiment 1.

The configuration of a watching system according to Embodiment 3 is a configuration in which, in the watching system according to Embodiment 1 described with reference to FIG. 7A, the biological signal processing devices 10A and 10B are replaced only by biological signal processing devices 30A and 30B (not shown) having the same configuration as the biological signal processing device 30, respectively. The other configuration is the same, and thus the description thereof is omitted. The operation of the watching system, that is, a watching method, according to Embodiment 3, will be described below.

(Description of Watching Method)

Figure 13:
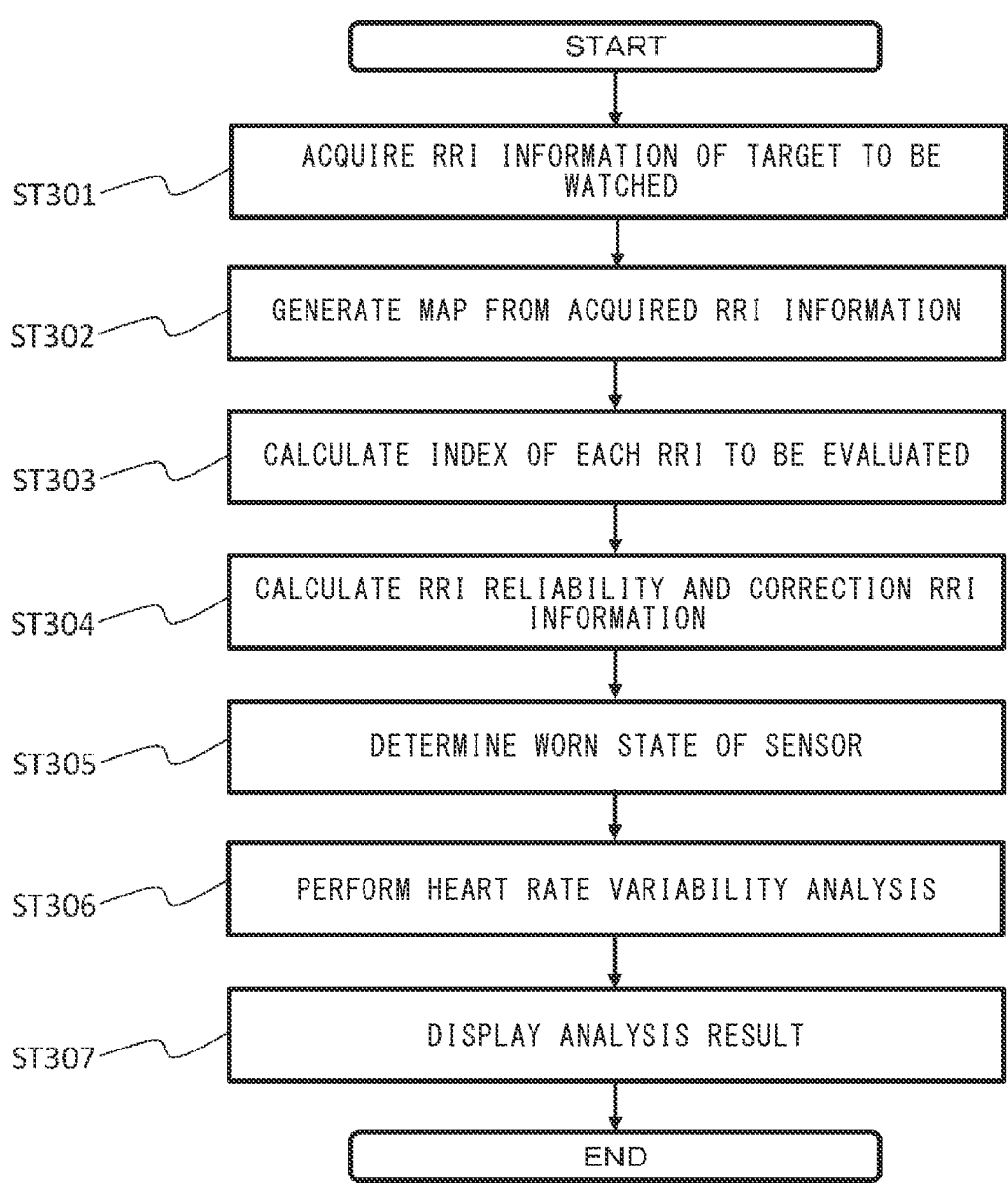
FIG. 13 is a flowchart showing the operation of a watching system according to Embodiment 3.

FIG. 13 is a flowchart showing the operation of the watching system according to Embodiment 3. In Embodiment 3, map generation is also performed in actual operation, so that pre-learning is not performed. That is, step ST301 to step ST307 are an actual operation process.

First, RRI information of the target to be watched is acquired (step ST301). The RRI information acquisition means 11 of the biological signal processing devices 30A and 30B acquires the RRI information 82A and 82B periodically outputted from the sensors 80A and 80B which detect biological signals of the targets to be watched. The RRI information 82A and 82B acquired by the biological signal processing devices 30A and 30B, respectively, are outputted as the RRI information 822 acquired in actual operation, to the index calculation means 34 and the map generation means 32 of the biological signal processing devices 30A and 30B.

Next, a map is generated from the RRI information acquired in step ST301 (step ST302). The map generation means 32 of the biological signal processing devices 30A and 30B each plot the points $P_k^*$ on the xy plane by the value of each RRI constituting the RRI information 822 acquired in actual operation, and classify each point $P_k^*$ as described above, to form a plurality of clusters. In addition, the cluster CL which intersects the straight line L0 is set as a valid cluster.

Next, the index of each RRI is calculated (step ST303). The index calculation means 34 assigns "1" to the points $P_k^*$ included in the valid cluster, and assigns "0" to the points $P_k^*$ included in an invalid cluster. Then, the indexes 83 of the RRIs constituting each point $P_k^*$ are calculated in the same manner as in Embodiment 1. The index calculation means 34 outputs the index 83 of each RRI to the reliability calculation means 15.

Next, RRI reliability and correction RRI information are calculated (step ST304). The reliability calculation means 15 of the biological signal processing devices 30A and 30B calculates the RRI reliability 85A and 85B from the index 83 of each RRI, and outputs the RRI reliability 85A and 85B to the RRI information correction means 16 of the biological signal processing devices 30A and 30B and the watching server 70. The RRI information correction means 16 corrects the RRI information 822 to be evaluated, by using the RRI reliability 85A and 85B. A specific correction method is as described above. The RRI information correction means 16 of the biological signal processing devices 30A and 30B outputs the correction RRI information 86A and 86B to the watching server 70.

Next, the worn state of the sensor 80 is determined (step ST305). The detailed description thereof is the same as that of step ST106 in Embodiment 1.

Next, the heart rate variability of the target to be watched is analyzed (step ST306). The detailed description thereof is the same as that of step ST107 in Embodiment 1.

Next, an analysis result is displayed (step ST307). The detailed description thereof is the same as that of step ST108 in Embodiment 1.

The others are the same as in Embodiment 1, and thus the description thereof is omitted.

According to Embodiment 3, the reliability of the measurement state of the biological signal can be evaluated only from the RRI information acquired in actual operation, without performing pre-learning. More specifically, the RRI information acquired in actual operation is outputted to both the index calculation means and the map generation means without being divided into the RRI information in the normal state serving as a basis and the RRI information to be evaluated. The map generation means plots points on the xy plane, which is a feature space, on the basis of each RRI constituting the acquired RRI information, then classifies the plotted points into a plurality of clusters by clustering, and determines a valid cluster and an invalid cluster. There is a possibility that the RRIs acquired in actual operation include abnormal ones. However, a valid cluster is determined from among a plurality of clusters, different values are assigned on the basis of whether or not the points composed of the RRIs to be evaluated are included in the valid cluster, and the index of each RRI is calculated on the basis of this value, so that the acquired RRI information can be evaluated. In Embodiments 1 and 2, as a result of performing pre-learning, the state of the target to be watched can be analyzed in real time in actual operation. On the other hand, real-time analysis is not required for a purpose in which it is not necessary to monitor the state of the target to be watched in real time and the state is analyzed later, for example. According to Embodiment 3, the RRI information, collection of which is completed in actual operation, can be analyzed offline and can be separated into a section in which normal measurement has been successfully performed and a section in which normal measurement has not been successfully performed.

When a map storage means is provided in the biological signal processing device of Embodiment 3, the state of the target to be watched can be monitored in real time by storing map information of a map generated in first offline analysis, in the map storage means, and reproducing the map by using the map information stored in the map storage means, in the next analysis or later analysis.

Embodiment 4

Figure 14:
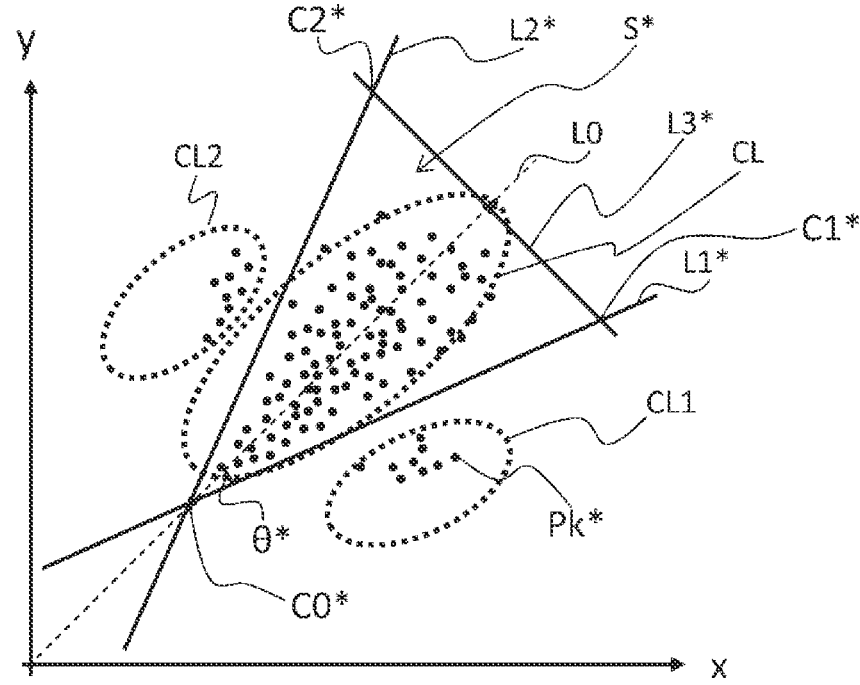
FIG. 14 illustrates a map and an index calculation method according to Embodiment 4.
Figure 15:
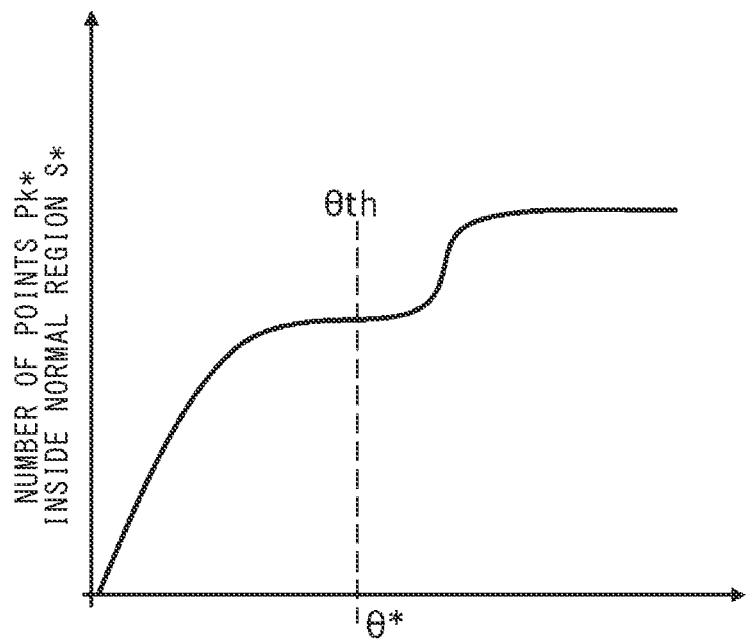
FIG. 15 shows the relationship between an angle $\theta^*$, which is the vertex angle of an isosceles triangle indicating a normal region according to Embodiment 4, and the number of points $P_k^*$ inside the normal region.

Next, Embodiment 4 will be described with reference to FIG. 14 and FIG. 15. Embodiment 4 is different from Embodiment 3 in a method for generating a map for evaluating the reliability of RRI information and a method for calculating the index of an RRI. FIG. 14 illustrates a map and an index calculation method according to Embodiment 4, and FIG. 15 shows the relationship between an angle $\theta^*$, which is the vertex angle of an isosceles triangle indicating a normal region according to Embodiment 4, and the number of points $P_k^*$ inside the normal region. In Embodiment 4, each point $P_k^*$ is plotted on the xy plane on the basis of the RRIs acquired in actual operation. In addition, the normal region is determined on the basis of the variation of the points $P_k^*$ within the normal region when the normal region is expanded, and the index of each RRI is calculated. Hereinafter, a detailed description will be given.

(Description of Map Generation Method)

The map generation means 32 determines the coordinates of the points $P_k^*$ from the RRIs constituting the RRI information 822 acquired in actual operation, according to equation (2), and plots the points $P_k^*$ on the xy plane. Here, it is assumed that N RRIs are acquired (N−1 points $P_k^*$ are plotted). The map generation means 32 classifies each point $P_k$* in the same manner as in Embodiment 3, to form a plurality of clusters, that is, point groups. In the example shown in FIG. 14, three clusters (clusters CL, CL1, and CL2) are formed. Next, among the formed clusters, a cluster that intersects a straight line L0 is set as a valid cluster, and a cluster that does not intersect the straight line L0 is set as an invalid cluster. Next, with a straight line L0 (y=x) as an axis of symmetry, two straight lines, a straight line L1* and a straight line L2* which intersect the straight line L0 at an intersection point C0* and whose angles with respect to the straight line L0 is θ*, are drawn. Furthermore, a straight line L3* which has a gradient of −1 and which intersects the straight line L1* and the straight line L2* at an intersection point C1* and an intersection point C2*, respectively, is drawn. A region surrounded by the straight line L1*, the straight line L2*, and the straight line L3* is set as a normal region S*. The position of the intersection point C0* and the initial positions (positions at θ*=0) of the intersection points C1* and C2* are determined in advance on the basis of the physiological findings.

The map generation means 32 makes θ* variable and gradually increases the value of θ* with an initial value as 0. In addition, the map generation means 32 counts the number of points $P_k$* inside the normal region S* while increasing the value of θ*. As shown in FIG. 15, when the value of θ* is increased from 0, the number of points $P_k$* inside the normal region S* increases, but the increase in the number of points $P_k$* becomes almost zero at a certain value θth. This means that the boundary of the normal region S* has been reached between the cluster CL which is a valid cluster and the clusters CL1 and CL2 which are invalid clusters. The map generation means 32 determines θth as a boundary value, and sets the normal region S*. The set normal region S* corresponds to the case where θ*=θth in FIG. 14, and all the points $P_k$* constituting the cluster CL which is a valid cluster are placed inside the normal region S* or on the boundary of the normal region S*. Therefore, the setting of the normal region S* is also the setting of the boundary between the valid cluster and each invalid cluster. In Embodiment 4, one in which the normal region S* is set on the xy plane which is a feature space is defined as a "map".

Since the normal region S* is determined by the straight lines L1*, L2*, and L3* when θ*=θth, the mathematical formulas indicating these straight lines are the map information 84 in Embodiment 4. In addition, since the normal region S* is also determined by θth and the intersection points C0*, C1*, and C2*, θth and the intersection points C0*, C1*, and C2* may be the map information 84. That is, similar to Embodiment 2, the map information of Embodiment 4 also may include a mathematical formula indicating the boundary of the normal region S* which is the map, or a coefficient determining the mathematical formula.

In the example shown in FIG. 14, the shape of the normal region S* is an isosceles triangle, but similar to the normal region S of Embodiment 2, the geometric shape of the normal region S* is not limited. In addition, the normal region S* can also be determined even in the case where the feature space is three-dimensional.

If there are many abnormal values, there is a possibility that the valid cluster and the invalid cluster cannot be necessarily separated from each other. In this case, even when θ* is increased, the number of points $P_k$* inside the normal region S* continues to increase permanently, so that the normal region S* cannot be determined. It is considered that, in view of such a possibility, abnormality detection indicating that there are too many abnormal values in the acquired RRIs when θ* reaches a value having a predetermined magnitude is performed. It is considered that when abnormality detection is performed in map generation, the RRI information 82 is acquired again and map generation is performed again.

(Description of Index Calculation Method)

The index calculation means 14 compares each point $P_k$* with the map information 84, assigns "1" to the points $P_k$* that are within the determined normal region S*, and assigns "0" to the points $P_k$* that are outside the determined normal region S*. Then, the index calculation means 14 calculates the indexes 83 of the RRIs constituting each point $P_k$*, in the same manner as in Embodiment 2. The index calculation means 14 outputs the index 83 of each RRI to the reliability calculation means 15.

The others are the same as in Embodiment 3, and thus the description thereof is omitted.

In Embodiment 4 as well, similar to Embodiment 2, potential information in which "1" is set for the inside of the normal region S* and "0" is set for the outside of the normal region S* is set in map generation, and one obtained by adding the potential information to the feature space may be used as a map. In this case, the map information 84 includes the above potential information. In addition, in index calculation, a value of "0" or "1" may be assigned to each point $P_k$* according to the position of the point $P_k$* and the above potential information.

According to Embodiment 4, the same advantageous effects as those of Embodiment 3 can be achieved.

Although the disclosure is described above in terms of various exemplary embodiments and implementations, it should be understood that the various features, aspects, and functionality described in one or more of the individual embodiments are not limited in their applicability to the particular embodiment with which they are described, but instead can be applied, alone or in various combinations to one or more of the embodiments of the disclosure.

It is therefore understood that numerous modifications which have not been exemplified can be devised without departing from the scope of the present disclosure. For example, at least one of the constituent components may be modified, added, or eliminated. At least one of the constituent components mentioned in at least one of the preferred embodiments may be selected and combined with the constituent components mentioned in another preferred embodiment.

DESCRIPTION OF THE REFERENCE CHARACTERS

10, 10A, 10B, 30 biological signal processing device
11 RRI information acquisition means
12, 32 map generation means
13 map storage means
14, 34 index calculation means
15 reliability calculation means
16 RRI information correction means
70, 701 watching server
715 biological signal processing means
72 heart rate variability analysis means
73 analysis result output means
80, 80A, 80B sensor
82, 82A, 82B, 821, 822 RRI information
83 index
84 map information
85, 85A, 85B RRI reliability
86, 86A, 86B correction RRI information 100, 101 watching system
CL, CL1, CL2 cluster
E analysis result
L0 straight line
P point group
$P_i$, $P_k^*$ point
S, S* normal region
The invention claimed is:

1. A biological signal processing device comprising:
a processor for executing a program; and
a memory or a hard disk for storing the program, wherein upon execution of the program, the processor is configured to:

i. acquire, from a body-worn sensor configured to calculate instantaneous heart rates (RRIs) of a biological signal of a target to be watched, first RRI information composed of a plurality of first RRIs arranged in time series, the processor being configured to acquire the first RRI information during a training mode;

ii. group the plurality of first RRIs about a straight line indicating a state where the first RRIs are constant in a feature space based on values of the first RRIs constituting the first RRI information, the feature space having a plurality of first points, wherein each first point includes a coordinate based on dimensions of the feature space and defined by a subset of the plurality of first RRIs in a normal state;

iii. store a grouping result of the first RRI information in the memory;

iv. acquire, from the body-worn sensor, second RRI information composed of a plurality of second RRIs arranged in time series, the second RRI information being obtained during an operating mode;

V. group the plurality of second RRIs in the feature space based on values of the second RRIs constituting the second RRI information, the feature space having a plurality of second points, wherein each second point includes coordinates designated by a subset of the plurality of second RRIs;

vi. calculate a first index indicating resemblance to heart rate variability of each second RRI to be evaluated by comparing a relationship between each second RRI with the grouping result of the first RRIs to determine a deviation amount;

vii. calculate a second index indicating a reliability of each second RRI to be evaluated based on an average of first indexes within a specified range of each second RRI;

viii. correct a target second RRI of the plurality of second RRIs when the second index of the target second RRI falls below a predetermined reliability threshold a specified number of times;

ix. actively monitor a heart rate variability of the target to be watched by iteratively performing steps iv to vii to determine the target's biological state; and x. issuing a notification to an external device based on an active monitoring result of the target to be watched.

2. The biological signal processing device according to claim 1, wherein the processor corrects the second RRI information by invalidating the second RRI whose RRI reliability is smaller than a predetermined threshold value, and deleting the invalidated second RRI from the second RRI information.

3. The biological signal processing device according to claim 2, wherein, when the RRI reliability consecutively falls below the threshold value a predetermined number of times, the processor invalidates the second RRIs whose RRI reliability falls below the threshold value.

4. The biological signal processing device according to claim 1, wherein the memory or the hard disk stores map information for reproducing the grouping result of first RRIs from the feature space, wherein the processor acquires the first RRI information including the first RRIs;

generates a map by determining the positions of the first points on the basis of the values of the first RRIs in the normal state acquired through the training mode, and outputs map information of the generated map to the memory or the hard disk.

5. The biological signal processing device according to claim 4, wherein the map information includes the coordinate of each first point constituting a point group which intersects the normal, and the processor calculates the index on the basis of a degree of deviation between the point group and one or more second points.

6. The biological signal processing device according to claim 4, wherein the map information includes information of a mathematical formula representing a boundary of a normal region, a point group which intersects a straight line indicating a state where the first RRIs are constant within the feature space is located on the boundary of or inside the normal region, and the processor calculates the index on the basis of whether or not one or more second points are on the boundary of or inside the normal region.

7. The biological signal processing device according to claim 6, wherein the feature space is a two-dimensional plane, and the normal region has an isosceles triangle shape with the straight line as an axis of symmetry.

8. The biological signal processing device according to claim 1, wherein the processor acquires the second RRI information including the second RRIs in the normal state, in actual operation, and generates the map by determining the positions of the second points on the basis of the values of the second RRIs in the normal state acquired in the actual operation.

9. The biological signal processing device according to claim 8, wherein the first points constitute a point group which intersects a straight line indicating a state where the first RRIs are constant within the feature space, and the processor calculates the index on the basis of whether or not the second point is included in the point group.

10. The biological signal processing device according to claim 8, wherein the first points constitute a point group which intersects a straight line indicating a state where the first RRIs are constant within the feature space, and the processor calculates the index on the basis of whether or not the second point is on a boundary of or inside a normal region, the point group is located on the boundary of or inside the normal region.

11. The biological signal processing device according to claim 10, wherein
the feature space is a two-dimensional plane, and
the normal region has an isosceles triangle shape with the straight line as an axis of symmetry.

12. The biological signal processing device according to claim 8, wherein the memory or the hard disk stores map information for reproducing the map from the feature space, wherein
the processor outputs the map information of the generated map to the memory or the hard disk.

13. A watching system comprising:
a body-worn sensor configured to calculate RRIs of a biological signal of a target to be watched;
a processor configured to communicate with the body-worn sensor and for executing a program; and
a memory or a hard disk for storing the program, wherein upon execution of the program, the processor is configured to:
  i. acquire first RRI information composed of a plurality of first RRIs arranged in time series;
  ii. group a plurality of first points about a straight line indicating a state where the first RRIs are constant in a feature space, the plurality of first points having positions that are determined on the basis of values of the first RRIs among the first RRIs constituting the first RRI information, and generate a map from the feature space on the basis of a grouping result of the plurality of first points, wherein each first point includes a coordinate based on dimensions of the feature space and defined by a subset of the plurality of first RRIs in a normal state;
  iii. store a grouping result of the first RRI information in the memory;
  iv. acquire second RRI information composed of a plurality of second RRIs arranged in time series;
  v. compare a second point whose coordinates are determined by a value of a subset of second RRI to be evaluated with the grouping result of the first RRIs in the feature space, and calculate a first index indicating resemblance to heart rate variability of each second RRI to be evaluated on the basis of a relationship between the second point and the with the grouping result of the first RRIs to determine a deviation amount;
  vi. calculate a second index indicating a reliability of each second RRI to be evaluated based on an average of first indexes within a specified range of each second RRI;
  vii. correct a target second RRI of the plurality of second RRIs when the second index of the target second RRI falls below a predetermined reliability threshold a specified number of times;
  viii. actively monitor a heart rate variability of the target to be watched by iteratively performing steps iv to vii to determine the target's biological state; and
  ix. issuing a notification to an external device based on an active monitoring result of the target to be watched.

14. The watching system according to claim 13, wherein the processor evaluates a worn state of the body-worn sensor worn by of the target to be watched, on the basis of the RRI reliability.

15. A watching method comprising:
a step of acquiring first RRIs of a biological signal of a target to be watched, by a body-worn sensor, and acquiring RRI information composed of a plurality of the RRIs arranged in time series;
a step of grouping a plurality of first points whose positions are determined on the basis of values of the first RRIs among the plurality of the first RRIs, on a feature space, and generating a map from the feature space on the basis of the plurality of first points, wherein each first point includes a coordinate based on dimensions of the feature space and defined by a subset of the plurality of first RRIs in a normal state;
a step of acquiring second RRIs of a biological signal of a target to be watched, by the body-worn sensor, and acquiring second RRI information composed of a plurality of the second RRIs arranged in time series;
a step of comparing a second point whose coordinates are determined by a value of a subset of second RRI to be evaluated with a grouping result of the first RRIs in the feature space, and calculating a first index indicating resemblance to heart rate variability of each second RRI to be evaluated, on the basis of a relationship between the second point and the the grouping result of the first RRIs to determine a deviation amount;
a step of calculating a second index of each second RRI to be evaluated based on an average of the grouping of first indexes within a specified range of each second RRI;
a step of correcting a target second RRI of the plurality of second RRIs a target second RRI when the second index of the target second RRI falls below a predetermined reliability threshold a specified number of times;
a step of actively monitoring a heart rate variability of the target to be watched by iteratively performing steps iv to vii to determine the target's biological state; and
a step of issuing a notification to an external device based on an active monitoring result of the target to be watched.

16. The watching method according to claim 15, wherein a worn state of the body-worn sensor of the target to be watched is evaluated on the basis of the RRI reliability.

\* \* \* \* \*